US008221648B2

(12) United States Patent
Naasani

(10) Patent No.: US 8,221,648 B2
(45) Date of Patent: *Jul. 17, 2012

(54) FUNCTIONALIZED FLUORESCENT NANOCRYSTAL DETECTION SYSTEM

(75) Inventor: Imad Naasani, Manchester (GB)

(73) Assignee: Life Technologies Corporation, Carlsbad, CA (US)

( * ) Notice: Subject to any disclaimer, the term of this patent is extended or adjusted under 35 U.S.C. 154(b) by 42 days.

This patent is subject to a terminal disclaimer.

(21) Appl. No.: 12/551,991

(22) Filed: Sep. 1, 2009

(65) Prior Publication Data

US 2010/0105048 A1 Apr. 29, 2010

Related U.S. Application Data

(63) Continuation of application No. 11/130,567, filed on May 17, 2005, now abandoned.

(60) Provisional application No. 60/571,872, filed on May 17, 2004.

(51) Int. Cl.
C09K 11/08 (2006.01)
G01N 21/76 (2006.01)

(52) U.S. Cl. .................. 252/301.36; 436/172; 977/774; 977/902

(58) Field of Classification Search .................. None
See application file for complete search history.

(56) References Cited

U.S. PATENT DOCUMENTS

| | | | |
|---|---|---|---|
| 5,749,847 A | | 5/1998 | Zewert et al. |
| 5,804,380 A | * | 9/1998 | Harley et al. ..................... 435/6 |
| 6,326,144 B1 | | 12/2001 | Bawendi et al. |
| 6,761,877 B2 | | 7/2004 | Barbera-Guillem |
| 6,955,855 B2 | * | 10/2005 | Naasani ......................... 428/403 |
| 7,198,847 B2 | | 4/2007 | Naasani |
| 7,214,428 B2 | | 5/2007 | Naasani |
| 7,368,086 B2 | | 5/2008 | Naasani |
| 2002/0001716 A1 | * | 1/2002 | Barbera-Guillem ..... 428/402.24 |
| 2002/0082193 A1 | * | 6/2002 | Anderson et al. .................. 514/1 |
| 2003/0054396 A1 | * | 3/2003 | Weiner .............................. 435/6 |
| 2003/0059635 A1 | * | 3/2003 | Naasani ..................... 428/473.5 |
| 2004/0247861 A1 | | 12/2004 | Naasani |
| 2005/0112376 A1 | | 5/2005 | Naasani |

FOREIGN PATENT DOCUMENTS

WO WO-2005/010211 2/2005

OTHER PUBLICATIONS

Chan et al. One-step conjugation of biomolecules to luminescent nanocrystals. In Molecular Imaging: Reporters, Dyes, Markers, and Instrumentation, Darryl J. Bornhop, 2 Kai Licha, Editors, Proceedings of SPIE vol. 3924 (pp. 2-9) (2000).*
Patolsky et al. Lighting-up the dynamics of telomerization and DNA replication by CdSe-ZnS quantum dots. Journal of the American Chemical Society 125:13918-9 (2003).*
Patolsky et al. Supporting Information [online] Oct. 24, 2003 [retrieved on Nov. 22, 2010] retrieved from http://pubs.acs.org/doi/suppl/10.1021/ja035848c.*
Akiyama, M., et al. "Telornerase overexpression in K562 leukemia cells protects against apoptosis by serum", Cancer Letters 2002, p. 187-197.
Brody, E., et al. "Aptamers as Therapeutic and diagnostic agents", Reviews in Molecular Biotechnology 74: 2000, p. 5-13.
Castro, S."Fluorescent Staining Advances", Genetic Engineering News 19 (17):1999, p. 30.
Cocco, M., et al. "Specific Interactions of distamycin with G-quadruplex DNA", Nucleic Acids Research 31(11): 2003, p. 2944-2951.
Counter, C., et al. "Telornerase Activity in Normal Leukocytes and in Hematologic Malignancies", Blood 85(9): 1995, p. 2315-2320.
De-Yun, F., et al. "An improvement method for the detection of in situ telomerase activity: situ telomerase activity labeling," WJG 5(6): 1999, p. 535-537.
Fu, W., et al. "Anti-apoptotic Role of Telomerase in Pheochromocytoma Cells", The Journal of Biological Chemistry 274(11): 1999, p. 7264-7271.
Fujiwara, M., et al. "Telomerase Activity Significantly Correlates with Chromosome Alterations, Cell", The United States and Canadian Academy of Pathology 13(7):2000, p. 723.
Hines, M., et al. "Synthesis and Characterization of Strongly Luminescing ZnS-Capped CdSe Nanocrystals", J. Phys. Chem. 100( 2): 1996, p. 468-471.
Hoare, S., et al. "Lack of Telomerase RNA Gene hTERC Expression in Alternative Lengthening of Telomeres Cells is Associated with Methylation of the hTERC Promoter", Cancer Research 61: 2001, p. 27-32.
Hyama, E., et al. "Correlating Telomerase Activity Levels with Human Neuroblastoma Outcomes", Nature Medicine 1(3):1995, p. 249-255.
Kim, N., et al. "Specific Association of Human Telemerase Activity with Immortal Cells and Cancer", Science 266:1994.
Komata, T., et al. "Telomerase as a therapeutic target for malignant gliomas", Oncogene 21:2002, p. 656-663.
Langford, L., et al. "Telomerase activity in human brain tumors", Lancet 346:1995, p. 1267-68. Matthes, E., et al. "Telomerase protein rather than its RNA is the target ofphosphorothioate-modified oligonucleotides", Nucleic Acids Research 27(4):1999, p. 1152-1158.
Mills, A., et al. "Detection ofS-Phase cells in tissue sections by in situ DNA replication", Nature Cell Biology 2:2000, p. 244-245.
Morin, G., et al. "The Human Telemoere Terminal Transferase Enzyme is a Ribonucleoprotein that Synthesizes TTAGGG Repeats", Cell 59:1989, p. 521-529.
Mukai, S., et al. "2-5A Antisense Telomerase RNA Therapy for Intracranial Malignant Gliomas", Cancer Research 60:2000, p. 4461-4467.
Murray, C., et al. "Synthesis and characterization of nearly monodisperse CdE (E = sulfur, selenium, tellurium) semiconductor nanocrystallites", Journal of the American Chemical Society 115(19):1993, p. 8706-8715.

(Continued)

Primary Examiner — Samuel Woolwine

(57) ABSTRACT

The present invention include fluorescent nanocrystals which have high fluorescence intensity, are water soluble, exhibit physical and chemical stability, and whose spectral properties are detectably modified as the size of functional groups bonded to the nanocrystal surface change when contacted with target molecules in a sample. The molecules in the sample add to or reduce the size of functional groups on the fluorescent nanocrystal proportional to the activity and amount of the target molecules. The present invention may be used to detect telomerase in a sample.

24 Claims, 10 Drawing Sheets

OTHER PUBLICATIONS

Naasani, I., et al. "A Potent Telomerase Inhibitor Identified by Exploiting the Disease-oriented Sureening Program with Compare Analysis", *Cancer Research* 59:1999, p. 4004-4011.

Naasani, I. "Blocking Telomerase by Dietary Polyphenols is a Major Mechanism for Limiting the Growth of", *Cancer Research* 63: 2003, p. 824-830.

Park, Richard "Reports Anticipate Growth in Molecular Diagnostics", *IVD Technology* 2004, p. 1-2.

Russell, D., et al. "Pathology of Tumours of the Nervous System—Chapter 3: Tumours of Central Neuroepithelial Origin." Published by Williams and Wilkins in US, p. 83-350.

Schmidt, P., et al. "Detection of Activity of Telomerase in Tumor Cells Using Fiber Optical Biosensors", *Biosensors and Bioelectronics* 17: 2002, p. 1081-1087.

Shammas, M., et al. "Telomerase Inhibition and Cell Growth Arrest After Telomestain Treatment in Multiple Myeloma", *Clinical Cancer Research* 2004, p. 770-776.

Shay, J., et al. "A Survey of Telemerase Activity in Human Cancer", *European Journal of Cancer* 1997, p. 787-791.

Shay, J., et al. "Telomerase Activity in Human Cancer", *Current Opinion in Oncology* 1996, p. 66-71.

Sun, H., et al. "The Bloom's Syndrome Helicase Unwinds G4DNA", *The Journal of Biological Chemistry* 1998, p. 27587-27595.

Wallweber, G., et al. "Interaction of Human Telomerase with its Primer Substrate", *Biochemistry* 42: 2003, p. 589-600.

Willard, D., et al. "CdSe-ZnS Quantum Dots as Resonance Energy Transfer Donors in a Model Protein-Protein Binding Assay", *Nano Letters* 1(9): 2001, p. 469-474.

Zhu, J., et al. "Telomerase extends the lifespan of virus-transformed human cells without net telomere lengthening", *Proceedings of the National Academy of Sciences* (*PNAS*) 96 (7): 1999, p. 3723-3728.

* cited by examiner m~1-3
p~1-4
X=NH$_2$,SH,OH,COOH m~1-3
p~1-4
X=NH$_2$,SH,OH,COOH m~1-3
p~1-4
X=NH$_2$,SH,OH,COOH n~6-12
X=NH$_2$,SH,OH,COOH n~6-12
X=NH$_2$,SH,OH,COOH

SEQUENCE LISTING

```
<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: synthetic construct

<400> SEQUENCE: 1
accctaaccc taaccctaac cctaac                                              26

<210> SEQ ID NO 2
<211> LENGTH: 6
<212> TYPE: DNA
<213> ORGANISM: Homo sapien

<400> SEQUENCE: 2 tagggt                                                                    6

<210> SEQ ID NO 3
<211> LENGTH: 24
<212> TYPE: DNA
<213> ORGANISM: Artificial Sequence
<220> FEATURE:
<223> OTHER INFORMATION: synthetic construct

<400> SEQUENCE: 3 tttttaatc cgtcgagcag agtt                                                24

<210> SEQ ID NO 4
<211> LENGTH: 18
<212> TYPE: DNA
<213> ORGANISM: Artificial Sequence
<220> FEATURE:
<223> OTHER INFORMATION: synthetic construct

<400> SEQUENCE: 4
aatccgtcga gcagagtt                                                      18
```

FUNCTIONALIZED FLUORESCENT NANOCRYSTAL DETECTION SYSTEM

CROSS REFERENCE TO RELATED APPLICATIONS

This application is a continuation of U.S. patent application Ser. No. 11/130,567, filed May 17, 2005 now abandoned, which claims the benefit of and priority to U.S. Provisional Application Ser. No. 60/571,872 filed May 17, 2004, the contents of which are incorporated herein by reference in their entirety.

BACKGROUND

Cancer is characterized by a chaotic set of disorders where each specific cancer type presents a unique problem with respect to diagnosis, prognosis and treatment. In spite of recent progress in earlier stage detection and molecular medicine, relatively simple, reliable, non-invasive and universal cancer diagnostic technology is still lacking.

Telomerase, a specialized reverse transcriptase, has a salient role in the process of immortalization and tumorigenesis, and is therefore considered to be a hallmark for the presence of cancer. During the cell cycle progression of a normal cell, DNA polymerase completely duplicates the genomic DNA except on the very ends of the Chromosomes—the telomeres. As a consequence, the telomeric end shortens an average of 50-200 base pairs each time the cell divides. Because of this "telomere shortening phenomenon," normal diploid cells are "mortal" and have limited capacity to proliferate. Immortalized cells, on the other hand, overcome this obstacle through the use of special mechanisms which perform telomere maintenance.

In most tumors, the maintenance of telomeres is achieved through the expression of telomerase, which stabilizes and elongates telomeres by the de novo synthesis of telomeric DNA (Ref. 1). Telomerase activity has been identified in ~90% of human tumors but is absent in the majority of normal tissues. A high level of telomerase activity correlates with the degree of malignancy and the likelihood of tumor progression. Furthermore, there is accumulating evidence that telomerase functions as both a DNA repair and an anti-apoptotic enzyme in addition to its role in telomere maintenance. Together these findings validate the view that telomerase is an attractive target for therapeutic intervention, diagnosis and disease monitoring.

Present methods for the detection of telomerase activity are based on variations of the two-step PCR-based telomeric repeat amplification protocol (TRAP) assay. In this assay active telomerase from cell or tissue extracts adds telomeric repeats (TTAGGG) onto the 3' end of a synthetic telomerase substrate primer. This primer is then amplified using PCR. The PCR-amplified "products" are then detected on a polyacrylamide gel or measured by ELISA. The TRAP assay, however, has not been adopted as a routine clinical test because of its limitations: the material must be processed fresh due to enzyme lability; The assay requires the use of several different instruments and takes several hours to complete, making it an unattractive routine test; there is a high possibility that false positive results can be generated from unspecific amplification of mismatch products by PCR; and inhibition of the assay by PCR inhibitors can produce false negative results. These shortcomings presently limit the clinical applicability of the current telomerase activity detection methods.

Additionally, there remains a need for a nonisotopic detection system which results in generation of a signal comprising fluorescence emission of high intensity, can result in signal amplification, is not limited as to the chemical nature of the target molecule to be detected (e.g., versus detection of nucleic acid molecules only), can be used to bind molecular probes of various types (affinity molecules, oligonucleotides, nucleobases, and the like), and can result in simultaneous detection of more than one type of target molecule by utilizing a class of nonisotopic molecules that may be excited with a single excitation light source and with resultant fluorescence emissions with discrete fluorescence peaks that can be spectrally distinguished from each other (e.g., using detection means for fluorescence that is standard in the art).

SUMMARY

Embodiments of the present invention include fluorescent nanocrystals which have high fluorescence intensity, exhibit physical and chemical stability, and whose spectral properties are detectably modified as the size of one or more functional groups bonded to the nanocrystal surface change when contacted with target molecules in a sample. The molecules in the sample may be added to the one or more functional groups on the fluorescent nanocrystal, for example by a polymerization reaction or surface modification process which results in multiple groups, acceptors, donors, layers or material added to the nanocrystal functional groups or substrates. The molecules in the sample may remove portions of one or more functional groups or substrates from fluorescent nanocrystals by degradation. Examples of polymerization reactions for lengthening or growth surface groups include but are not limited to nucleic acid, protein, or carbohydrate synthesis and may be in vitro or in vivo. Examples of degradation reactions for shortening surface groups include but are not limited to enzyme degradation or cleavage of amino acids from proteins bonded to a fluorescent nanocrystal, or degradation of oligonucleotides by nucleases.

One embodiment of a composition may include one or more fluorescent nanocrystals with a coating material that can include imidazole-containing molecules bonded by an imidazole group of the molecule to the surface of the fluorescent nanocrystals. The fluorescent nanocrystal coating may further include a cross linking agent. One or more functional groups are bonded at a first end to the coating on the fluorescent nanocrystal while the second end of the one or more functional group extends outward from the fluorescent nanocrystal coating. The spectral properties, mobility, tumbling or a combination of these of the fluorescent nanocrystal can be modified by reaction, for example by sequential lengthening, shortening, or a change in mass, of one or more of the functional groups with one or more target molecules in a sample. The reaction of the functional groups with the target molecules may result in a change in the size or mass of the functional groups as molecules in the sample, which may be the same or different from the target molecule, are sequentially added or removed from one or more of the functional groups. The composition may include other groups such as but not limited to one or more fluorphores, acceptors, donors, or other moieties that can absorb energy emitted from the fluorescent nanocrystal or can excite the fluorescent nanocrystal, these groups are linked to the functional groups that are bonded to the coating material. The linked fluorphores or acceptors can absorb at least a portion of the fluorescent emission from the nanocrystal. The linked donors can excited the fluorescent nanocrystal. The functional groups on the coating of the fluorescent nanocrystals can react with target molecules in a sample. The functional groups can include polynucleotides, polypeptides, glycoproteins, polysaccharides, lipoproteins, portions of these, or combinations of these. In one embodiment of the fluorescent nanocrystal composition, the functional groups are telomerase primers bonded to the coating material; the primers bonded through a first end, the 5' end, to the coating of the nanocrystal, the second end of the primer, the 3' end, extending from the nanocrystal coating, where the spectral properties of the fluorescent nanocrystal are modified by elongation of the primers when telomerase molecules are present in the sample along with deoxynucleotides (dNTP's), fluorophore labeled dNTP's, or combinations of these.

The number of functional groups bonded to the coating on the fluorescent nanocrystals that can react with target or analyte molecules in the sample can be greater than about 25. In some embodiments, the number of functional groups bonded to the coating can be about 100 or more. In some embodiments, the number of functional groups bonded to the coating can be about 170 or more. The functional groups may include one or more fluorophores or acceptors that can absorb the fluorescent emission of the excited nanocrystals. The functional groups may include one or more donors that can excite fluorescent emission of the coated nanocrystals. In some embodiments, the functional groups can be bonded to a coating material comprising imidazole containing molecules bonded by an imidazole group of the molecule to the surface of the fluorescent nanocrystals. In some embodiments, the composition includes coated fluorescent nanocrystals that have a quantum yield of greater than 70%.

One embodiment of the invention is a method that can include the acts of contacting a sample with fluorescent nanocrystals, the fluorescent nanocrystals include a coating of imidazole-containing molecules bonded by one or more of the imidazole group to the surface of the fluorescent nanocrystals. The fluorescent nanocrystal coating may further include a cross linking agent. Functional groups are bonded to the coating material with a first end of the functional group bonded to the coating of the fluorescent nanocrystal and a second end of the functional group extending from the nanocrystal coating where the spectral properties, mobility, or a combination of these of the fluorescent nanocrystal are modified by reaction of one or more of the functional groups with one or more target molecules in a sample. The method further includes the act of correlating a change in the spectral properties, mobility, or a combination of these of the fluorescent nanocrystals in the sample with the reaction of one or more of the functional groups with one or more target molecules in the sample. The method can include correlating the change in the spectral properties, mobility, or a combination of these of the fluorescent nanocrystals in the sample to the number, activity, or concentration of target molecules in the sample.

The target molecule in the sample that results in a change in the spectral properties, mobility, or a combination of these of the fluorescent nanocrystal with the functional groups can include an enzyme or other catalyst where the reaction of the functional groups with the target molecule results in elongation, shortening, or a change in mass of the functional groups bonded to the coating on the fluorescent nanocrystals. The elongation or shortening can occur by the sequential removal or addition of multiple groups or moieties from one of more of the bound functional group. The reaction of functional groups with target molecules in the sample can result in the addition or removal of one or multiple fluorophores, acceptors, or donor moieties from functional groups bonded to the coating. Target molecules may include but are not limited to various nucleotides, amino acids, nucleic acids, proteins, glycoproteins, structural materials like collegens, and carbohydrates and fluorophore or donor linked versions of any of these.

In one embodiment of the method, the functional groups are telomerase primers bonded to the coating material; the primers bonded through a first end, the 5' end, to the coating of the nanocrystal, the second end, the 3' end, of the primers extending from the nanocrystal coating. A change in the spectral properties of the fluorescent nanocrystal are modified by elongation of the primers reacting with a sample comprising telomerase molecules and nucleotides. The reaction of the functional groups with the target molecules may result in a change in the size or mass of the functional groups as nucleotide molecules in the sample are sequentially added to one or multiple functional groups thereby growing the length of the functional groups. In one embodiment, one or more of the nucleotides in the sample further includes an acceptor label or donor label bonded to the nucleotide. The fluorescent nanocrystals combined with the sample can include one or more fluorophores, acceptors, or donors linked to the functional groups, the linked fluorphores, acceptors, or donors capable of exchanging energy with the linked fluorescent nanocrystal.

In one embodiment, fluorescent nanocrystals whose spectral properties are detectably modified as functional groups bonded to the nanocrystal surface grow and lengthen may be used for a rapid, non-invasive, fluorescence-based technique for the detection of human cancers. A detectable label or a biosensor can be made for the detection of telomerase, a hallmark enzyme for immortalization and tumorigenesis. A coating step results in organically coated nanocrystals that include imidazole groups bonded to the fluorescent nanocrystal to provide fluorescent nanocrystals that are water soluble and can be linked to biologically useful functional groups. Short strands of telomerase substrate DNA (TS) can be used as functional groups and may be conjugated to the coated FNCs having specific spectral characteristics. If telomerase activity is present in a sample of cells contacted with these primer functionalized nanocrystals, they can elongate TS primer strands on the FNC, resulting in a change in the spectral properties of the linked nanocrystal.

One embodiment of an apparatus can include a sample holder including fluorescent nanocrystals with a telomerase primer bonded to a coating, the coating includes imidazole containing molecules bonded to the fluorescent nanocrystal by an imidazole group. The apparatus can further include an energy source for exciting fluorescent emission of the nanocrystals and a detector for measuring the spectral properties of the excited nanocrystals.

In another embodiment, a method of detecting a telomerase can include combining fluorescent nanocrystals having telomerase substrate primers with a sample on with a lateral flow assay plate.

In another embodiment a kit for a fluorescent assay can include a vial of fluorescent nanocrystals having functional groups linked to a coating material. The functional groups can react with target molecules in a sample to modify the size or mass of the functional groups. The reaction can modify the functional groups by elongation, shortening, a change in mass, or a combination of these. Modification of the functional groups may be detected by a change in the spectral properties, mobility, or a combination of these of the fluorescent nanocrystals. In some embodiments, the functional groups are be bound to a coating on the fluorescent nanocrystals by imidazole-containing molecules bonded by an imidazole group of the coating molecule to the surface of the fluorescent nanocrystals. In some embodiments, the functionalized nanocrystals are stable above about 25° C. and preferably above about 37° C. In some embodiments the coated fluorescent nanocrystals include greater than about 25 functional groups and preferably greater than about 100 functional groups bonded to the coated fluorescent nanocrystal. The vial with the functionalized fluorescent nanocrystals may also contain reagent molecules, fluorphores, transfecting agents, excipients, or any combination of these. Optionally, the kit may contain separate vials with these components. The kit may include lateral flow assay strips.

The fluorescent nanocrystal composition in embodiments of the invention may further comprises a buffer and the composition can be held at a temperature of about 37° C. or greater. These compositions can be used in a method that includes the reaction of the functional groups with the target molecules in the sample at a temperature of about 37° C. or greater. In some embodiments, the fluorescent nanocrystal composition includes a transfecting agent that can be used to permeabilize cells or a transfecting agent that can encapsulate the functionalized nanocrystals and transport them into cells and where the functional groups bonded to the coating can be elongated or shortened by target molecules in the cells. The composition may further include cells to be tested for the presence or absence of target molecules.

The fluorescent nanocrystal compositions can be used to detect target molecules in a sample. For example, functionalized nanocrystals with telomerase primers can be used in a test for the detection of cancer, thus addressing a need in clinical diagnostics. The combination of the versatility and functionality of fluorescent nanocrystals with the universality of telomerase as a cancer marker offers the prospect of creating a powerful but user-friendly tool for the detection of a number of cancers. Because of their stability, high number of functional groups, and high quantum yield, sensing using these fluorescent nanocrystals can be made available for use in applications that involve large population screening, anti-cancer drug discovery and therapeutic drug monitoring.

Fluorescent nanocrystals functionalized for telomerase detection can be modified for adaptation to existing high throughput screening platforms. There are presently several commercially available high throughput reading instruments for 96-well fluorescence or polarization detection platforms. Flow cytometry analysis may be configured and used with functionalized nanocrystals with telomerase primers in the diagnosis of different types of leukemia.

The above and other objects, features, and advantages of these embodiments will be apparent in the following DETAILED DESCRIPTION when read in conjugation with accompanying drawings in which reference numerals denote the same or similar parts throughout the several illustrated views and embodiments.

DESCRIPTION OF THE DRAWINGS

The file of this patent contains at least one photograph or drawing executed in color. Copies of this patent with color drawing(s) or photograph(s) will be provided by the Patent and Trademark Office upon request and payment of necessary fee.

FIG. 8 illustrates the modification of spectral properties of fluorescent nanocrystals with a change or modification in the size or mass of the functional group using DNA.

DESCRIPTION

Figure 1A:
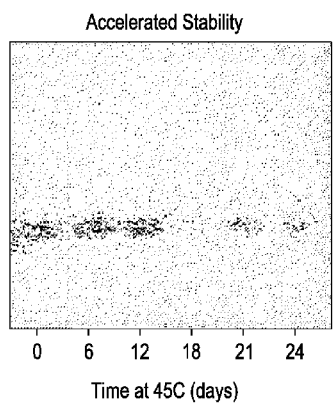
FIG. 1 Show test results that illustrate the long-term storage stability of coated fluorescent nanocrystals that may be used in embodiments of the present invention.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural references unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described.

All publications mentioned herein are incorporated by reference. Nothing herein is to be construed as an admission that the invention is not entitled to antedate such disclosure by virtue of prior invention.

"Optional" or "optionally" means that the subsequently described event or circumstance may or may not occur, and that the description includes instances where the event occurs or material is present and instances where the event does not occur or where the material is not present.

Throughout the specification of the application, various terms are used such as "primary", "secondary", "first", "second", and the like. These terms are words of convenience in order to distinguish between different elements, and such terms are not intended to be limiting as to how the different elements may be utilized.

Semiconductor nanocrystals are now being evaluated as a promising tool of nonisotopic detection to replace conventional fluorescent molecules. Since the spectral emission characteristics of nanocrystals are a function of their size, nanocrystals produced in a narrow size distribution can be excited to emit at discrete fluorescence peak of narrow bandwidth. Advantages of fluorescent nanocrystals include the ability to control the spectral characteristics of nanocrystals such as narrow bandwidth, discrete peak emission wavelengths, and the ability to use a single wavelength or narrow wavelength band to excite an array of nanocrystals with different peak emissions. Another advantage of the fluorescent nanocrystals compared to fluorescent dyes is their resistance toward photobleaching under intensive light sources.

A continuous flow process as detailed in U.S. Pat. No. 6,179,912, the disclosure of which is herein incorporated by reference in its entirety, or a batch method can be used for the production of fluorescent semiconductor nanocrystals using high or low temperature processing conditions as necessary. The appropriate method is one which permits subsequent surface functionalization or coating and provides crystals with a narrow FWHM, preferably less than about 50 nm, more preferably less than about 30 nm. In some embodiments, approximately monodisperse (less that about ±3% size variation per wavelength) fluorescent nanocrystals in selected wavelengths from about 400 to about 800 nm or higher with FWHM excitation/emission bandwidths of about 30 nm or narrower are used for coating and functionalization. In some embodiments using a continuous flow process, fluorescent nanocrystal made having a run-to-run reproducibility with a standard deviation of about ±1.6 nm, or within about ±0.3% are used for coating and functionalization.

Fluorescent nanocrystals (FNCs) that can be used in some embodiments of the invention may include nanocrystals comprising semiconductor nanocrystals, doped metal oxide nanocrystals, and core shell variations of these. Semiconductor nanocrystals are quantum dots (also known as crystallite semiconductors) that can be comprised of a core comprised of at least one of a Group II-VI semiconductor material (of which ZnS, HgS, and CdSe are illustrative examples), or a Group III-V semiconductor material (of which GaAs is an illustrative example), or a Group IV semiconductor nanocrystal, or a combination thereof. These core semiconductor nanocrystals may further comprise and be passivated with a "shell" or capping layer of material uniformly deposited on the core. The capping layer material may be comprised of an inorganic material with a higher band gap than the core nanocrystal. Inorganic materials typically used to passivate CdX (X=S, Se, Te) core nanocrystals are preferably comprised of YZ where "Y" is Cd, Hg, or Zn and "Z" is S, Se, or Te. Core CdX nanocrystals with a YZ shell. The fluorescent nanocrystals, core or capped, may be coated with a composition that includes compounds with an imidazole group bound to the fluorescent nanocrystal through an imidazole group of the compound. The coating may also include alkyl phosphine-containing compounds. The size of the core of the semiconductor nanocrystal correlates with the spectral range of emission. In some embodiments, the semiconductor nanocrystals are produced using a continuous flow process and system and may have a particle size that varies by less than ±10% in the average particle size (as measured by diameter) in the range of approximately 1 nanometer (nm) to approximately 20 nm. Semiconductor nanocrystals useful in the practice of various embodiments may also be characterized in that the dimensions of the nanocrystals are comparable or smaller than their bulk exciton diameter so that they exhibit size dependent optoelectronic properties and when excited can emit electromagnetic radiation in the visible or infrared ranges.

Figure 1B:
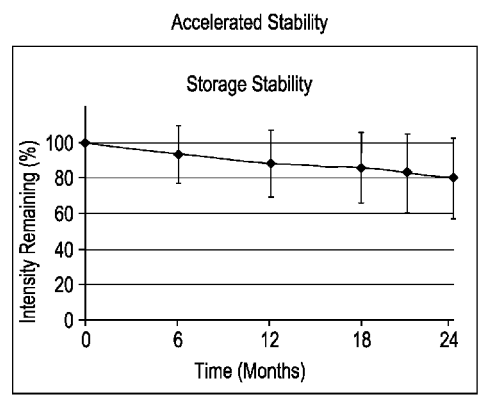
Figure 1C:
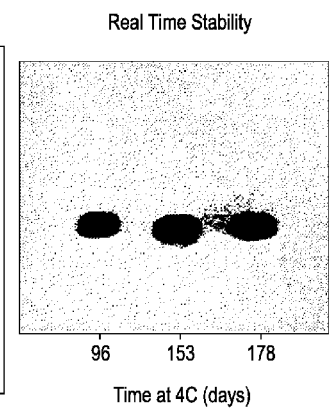

The stability of coated fluorescent nanocrystals, fluorescent intensity and aggregation, may be determined in an accelerated shelf life test. Preferably for use in sensors and assays, coated FNCs, or coated FNC's with reactive functionalities (those that can change size or mass) can be stored for extended periods of time. For example, imidazole bound molecules in a coating on fluorescent nanocrystals were stored for up to 24 days at 45° C. without light protection, and then run on an agarose gel FIG. 1A. The fluorescence intensity was quantified using NIH Image and analyzed by means of an Arrhenius equation to determine the projected 4° C. shelf life as illustrated in FIG. 1B. In this test, the imidazole coated FNCs maintained their fluorescence over the equivalent of 18 months at 4° C. and only diminish 20% over the equivalent of two years in storage. In a real-time study, coated FNCs were stable when stored at 4° C. without protection from light exposure. The intensity of the fluorescence (as indicated by the brightness of the band on an agarose gel) did not diminish over a six-month storage period. The material did not aggregate or lose its surface charge (shown by the tightness of the bands in FIG. 1C). Preferably the coated fluorescent nanocrystal used in embodiments of compositions and methods of the present invention are at least as stable as these.

The coated fluorescent nanocrystals and coated fluorescent nanocrystals with functional groups bonded to the coating can be used with a variety of buffers and at different pH. They are water soluble and are stable and fluorescent in a wide range of biological buffers (PBS, TBS, NaCl (<125 mM), Borate, MES, Casein) and a range of pH conditions such as from about pH 2 to about pH 10, and preferably about pH 6 to about pH 10. This advantageously enables these coated and functionalized fluorescent nanocrystals to be incorporated into a variety of established biological assays without altering the protocols.

In biological applications, the amount of coated fluorescent nanocrystals or coated fluorescent nanocrystals with bound functional groups that may be contacted with cells, tissue, or a patient, is an amounts that is not harmful. Coated fluorescent nanocrystals may be contacted with cells in culture in μg/ml concentrations. The concentration of coated fluorescent nanocrystals or coated fluorescent nanocrystals with functional groups that may be safely used can be determined by culturing cells, for example CHO-K1 cells with varying concentrations of coated fluorescent nanocrystals for 24 hours in chamber slides. After the culture period, the number of dead cells can be quantified using a trypan blue dye exclusion assay.

Fluorescent nanocrystals can be made water-soluble. "Water-soluble" refers to coated fluorescent nanocrystals that are sufficiently soluble or suspendable in an aqueous solution, such as in water, water-based solutions, buffer solutions, or other fluids used in biological or molecular detection systems. Coated fluorescent nanocrystal particles and functional surfaces may also be characterized by their ability to be wet by a fluid. The fluid may be water or a solution of water and other liquids like ethanol. One method to impart water-solubility or wettability to semiconductor nanocrystals (e.g., CdX core/YZ shell nanocrystals) is to exchange the overcoating layer of TOP or TOPO with a coating, or "capping compound", which will impart some water-solubility. In some embodiments of the coated fluorescent nanocrystals, the coating includes imidazole containing molecules bonded by imidazole groups to the fluorescent nanocrystal. Depending on the nature of the coating compound, some coated semiconductor nanocrystals which have been reported as water-soluble may have limited stability in an aqueous solution, particularly when exposed to air (oxygen) and/or light. For example, oxygen and light can cause mercapto-based monothiols used in capping and passivation of nanocrystals to become catalytically oxidized, thereby forming disulfides which can destabilize the attachment of the coating.

Functionalized fluorescent nanocrystals in various embodiments are soluble in aqueous solutions and other fluids depending upon the ligands comprising the coating or functional groups bonded to the coating. For example, they may be soluble in water, water and isopropyl alcohol mixtures or liquids with surface tensions below about 80 dynes/cm, and preferably in the range from about 30-73 dynes/cm. The solvent or solvent mixture used to solublize or suspend the functionalized nanocrystals may have a surface energy which is about the same as the surface energy of the particular coating material of the functionalized nanocrystal. The surface energy of coating can vary with the molecular properties and amount of the ligands in the coating material; preferably the moiety of the coating material is compatible, soluble and chemically stable, with the fluids it is contacted with. Chemically stable moieties of the coating material maintain the fluorescent emission intensity over time depending upon the application of the functionalized fluorescent nanocrystals. The functionalized nanocrystals (FNC) in various embodiments described were soluble in water, mixtures of water and glycerol (50%), water and ethanol (10%), water and methanol (50%; ~35 dynes/cm), water and DMSO (50%), water and polyethylene glycol 200 (50%), and water and isopropyl alcohol (50%). The FNC were also soluble in 100% of glycerol, and isopropyl alcohol particularly after adding other solvents to isopropyl alcohol In various embodiments, the fluorescent nanocrystal may have a coating that includes one or more imidazole-containing compounds bound by an imidazole group to the fluorescent nanocrystal surface. The coating may further include an alkyl phosphine-containing compound. The coated fluorescent nanocrystals may further comprise chemical or physical cross-linking of the coating material comprising imidazole-containing compound and alkyl phosphine-containing compound to promote further stabilization of the coating on the fluorescent nanocrystals. Chemical cross-linking can be achieved by using methods and reagents known in the art which may include, but are not limited to, formaldehyde, glutaraldehyde, acrolein, 1,6-hexane-bis-vinylsulfone, putrescine, alkyl diamines, and other organic triamines or polyamines. Physical cross-linking and/or curing can also be achieved by using methods known in the art which may include, but are not limited to, ultraviolet irradiation, microwave treatment, heat treatment, and radiation.

Molecules and reactive functionalities may be chemically or physically connected to the nanocrystal, operably bound, by a fusion or bond or an association, of sufficient stability for the purposes of use. A coating may comprise one or more functional groups that can be molecules or ligands. As known to those skilled in the art, and as will be more apparent by the following embodiments, there are several methods and compositions in which two or more molecules may be operably bound to the nanocrystals utilizing reactive functionalities. Reactive functionalities may include, bifunctional reagents (e.g., homobifunctional or heterobifunctional), biotin, avidin, free chemical groups (e.g., carboxyl, hydroxyl, amino, amine, sulfo, and the like), and reactive chemical groups (reactive with free chemical groups). As known to those skilled in the art, the bond may compromise, but is not limited to, one or more of: covalent, ionic, hydrogen, van der Waals, and the like.

Imidazole compounds in a coating include heterocyclic or heteroaromatic molecule or ligand that has at least one imidazole group (e.g., imidazole ring) available for binding with the fluorescent nanocrystal or capping compound a metal such as zinc, cadmium, gallium, or other metal cation, or substrate containing such cation. In that respect, preferably at least one imidazole moiety is in a terminal position with respect to the structure of the molecule. The imidazole containing compound operably bonds to the fluorescent nanocrystal through the imidazole group. Generally, imidazole ring nitrogens serve as coordinating ligand to operably bind a metal ion such as zinc or cadmium. In a preferred embodiment, the imidazole-containing compound comprises additional reactive functionalities such as an amino acid, or two or more amino acids joined together (e.g., known in the art as "peptidyl" or "oligopeptide"), which may include, but is not limited to, histidine, carnosine, anserine, baleine, homocarnosine, histidylphenylalanine, cyclo-histidylphenylalanine, 5-amino-4-imidazolecarboxamide, histidylleucine, 2-mercaptoimidazole, boc-histidine hydrazide, histidinol, 1-methylhistidine, 3-methylhistidine, imidazolysine, imidazole-containing ornithine (e.g., 5-methylimidazolone), imidazole-containing alanine (e.g., (beta)-(2-imidazolyl)-L(alpha) alanine), carcinine, histamine, histidyl glycine, glycyl histidine and the like.

Amino acids include compound or ligand containing at least one amino group and at least one carboxyl group. As known in the art, an amino group may occur at the position adjacent to a carboxyl group, or may occur at any location, for example β and γ amino acids, along the amino acid molecule. In addition to at least one imidazole moiety, the amino acid may further comprise one or more additional reactive functionalities, for example amino, thiol, carboxyl, carboxamide, or others. The amino acid may be a naturally occurring amino acid, a synthetic amino acid, a modified amino acid, an amino acid derivative, an amino acid precursor, in D (dextro) form, or in L (levo) form. Examples of derivatives may include, but are not limited to, an n-methylated derivative, amide, or ester, as known in the art. Consistent with the functionality of the amino acid, it acts as a coating for the fluorescent nanocrystals and may impart water-solubility, buffer sufficiently in a pH range between about pH 2 to about pH 10 and preferably from pH 6 to about pH 10, functions as a coat which can increase fluorescence intensity, or have one or more reactive functionalities that may be used to operably bind at least one molecular probe or functional group. An amino acids of the aforementioned amino acids may be used in a preferred embodiment, and a preferred amino acid may be used separately in the composition of the present invention to the exclusion of amino acids other than the preferred amino acid. In some embodiments, the coating on the fluorescent nanocrystals includes glycyl histidine, which is an imidazole-containing compound.

By the term "alkyl phosphine cross-linking compound" is meant to refer to a molecule or ligand that has at least one phosphine group available for binding or chelating a non metal such as Se, S or other non metals, or substrate containing such atoms, and has at least one functional group (e.g., hydroxyl, amino, thiol, carboxyl, carboxamide, etc) with ability to react with neighboring molecules. In that respect, preferably at least one phosphine moiety is in a terminal position with respect to the structure of the molecule. Generally, phosphine moieties frequently serve as coordinating ligand to operably bind with the fluorescent nanocrystal or capping compound a non metal or ion such as Se or S. In a preferred embodiment, the alkyl phosphine-containing compound comprises a phosphine group, or two or more phosphine groups joined together (e.g., in a polymeric form), which may include, but is not limited to, hydroxymethylphosphine compounds, and the like. Alkyl phosphine-containing compounds may be synthesized using methods known in the art (see, e.g., Tsiavaliaris et al., 2001, Synlett. 3: 391-393, Hoffman et al, 2001, Bioconjug Chem 12: 354-363, U.S. Pat. No. 5,948,386). As known in the art, an alkyl phosphine-containing compound may further comprise one or more additional reactive functionalities, for example, hydroxyl, amino, thiol, carboxyl, carboxamide, or others. Examples of derivatives may include, but are not limited to, a hydroxy methyl phosphine derivative, amide, or ester, as known in the art, and where consistent with the functions of the alkyl phosphine as a coating as described herein (e.g., imparts water-solubility, buffers sufficiently in a pH range between about pH 2 and about pH 10, preferably from about pH 6 to about pH 10, functions as a coat and cross-linker which can increase stability and fluorescence intensity, or has one or more reactive functionalities that may be used to operably bind a molecular probe or functional group. An alkyl phosphine of the aforementioned derivatives may be used in a preferred embodiment, and a preferred alkylphosphine may be used separately in the composition of the present invention to the exclusion of alkyl phosphines other than the preferred alkyl phosphine. Tris(hydroxy methyl) phosphine and beta-[Tris (hydroxymethyl)phosphino]propionic acid are particularly preferred alkyl phosphine-containing compound for coating, stabilizing and functionalizing fluorescent nanocrystals according to the present invention. Also known in the art is that cross-linked alkyl phosphine-containing compounds have additional ability to operably bind to metal atoms and/or ions such as zinc and cadmium. In this respect functionalized isocyanates or alkyl cyanoacrylates may also be useful for cross-linking ligands and adduct formation with fluorescent nanocrystals in the practice of this invention.

The nanocrystal coated with the coating material of the present invention may further comprise an additional layer or functional groups bonded to the surface of the coating material. The moieties of the layer may be organic or inorganic and provide chemical compatibility, reactivity, or solubility with a fluid or suspension media. For example, additional amino acids like arginine may be coupled to the imidazole-containing group in the coating material, or short chain polymer or peptide sequences like arginine-glycine-serine, with the serine hydroxyl moiety interacting with the suspending medium, may be used. Amino acids and other such groups will have an affinity for the amino acid portion of the imidazole containing group of the coating material and may be reacted with them using standard coupling reactions. The addition of amino acids by these coupling reactions elongates the moieties and result in changes in spectral properties of the fluorescent nanocrystal. In general, one or more functional groups can be bonded at a first end to the coating on the fluorescent nanocrystal while the second end of the functional group extends outward from the fluorescent nanocrystal coating. In some embodiments, the functional group is bonded to reactive functionalities of an imidazole bound imidazole containing coating. The spectral properties, physical properties like mobility or tumbling, or a combination of these of the coated fluorescent nanocrystal can be modified by sequential reaction, for example by sequentially lengthening, shortening, or a change in mass, of one or more of the functional groups by sequential reaction with one or more target molecules in a sample. One or more of the functional groups are sequentially lengthened by addition of multiple molecules, which may be the same or different, to a functional group, or sequentially shortened by sequential removal of multiple moieties from a functional group. The functional groups may include one or more fluorphores, acceptors, or donors linked to the functional groups that are bonded to the coating material. The linked fluorphores and or acceptors, which can be dyes like Texas-Red or other fluorescent nanocrystal, can absorb at least a portion of the fluorescent emission from an excited fluorescent nanocrystal to which it is bound. Donors can be moieties that can excite the fluorescent nanocrystal to fluoresce and can be linked to through the functional groups and can include beta emitters or other fluorescent nanocrystals. The functional groups can include polynucleotides, polypeptides, glycoproteins, polysaccharides, lipoproteins, portions of these, or combinations of these.

Figure 3:
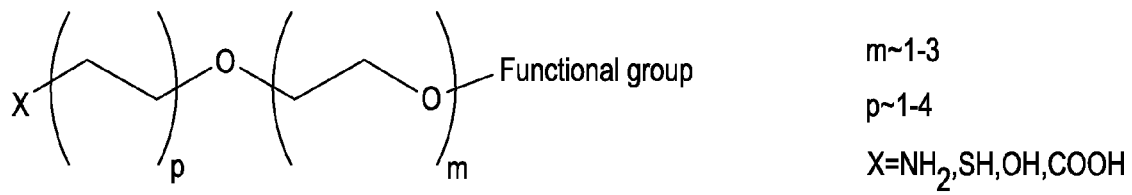
FIG. 3 illustrates non-limiting embodiments functional groups that can be bonded to the coated fluorescent nanocrystals and that can react sequentially with target molecules in a sample to modify the size or mass of the functional group.
Figure 3:
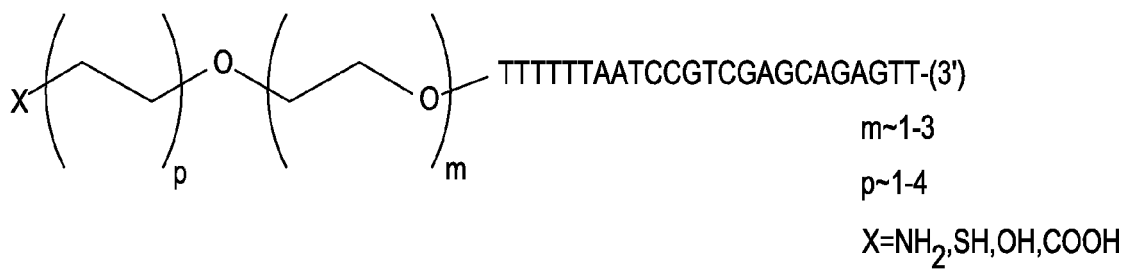
Figure 3:
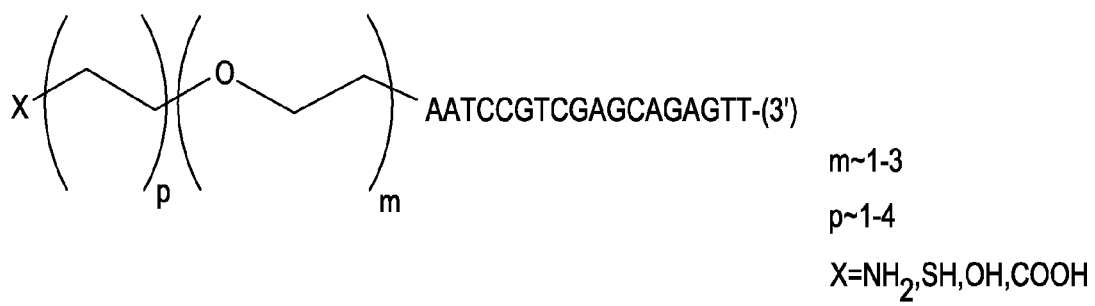
Figure 3:
Figure 3:
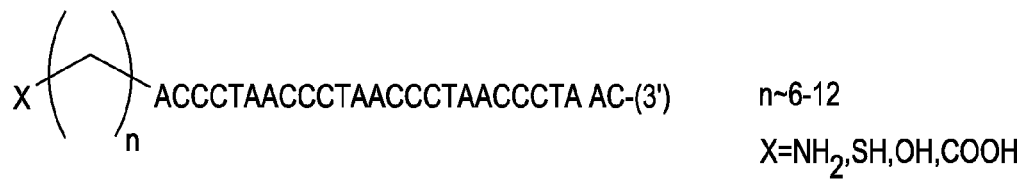
Figure 3:
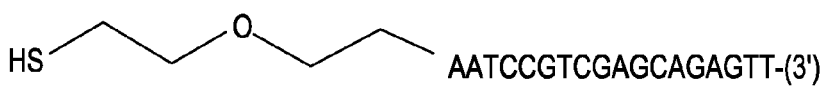

One or more functional groups linked to a coating having imidazole groups bound to a fluorescent nanocrystal can be illustrated by DNA oligonucleotides be linked to FNCs. Oligonucleotides with varying numbers of bases equipped with an amine, or other suitable reactive group, modified linker arm at the 5' end can be conjugated or bonded to reactive functionalities of imidazole bound compounds coating the surface of fluorescent nanocrystals. A non-limiting example of a functional group is a 26-base oligonucleotide, 5'-ACCCTAACCCTAACCCTAACCCTAAC-3' (SEQ ID NO:1) equipped with an amine modified linker arm of 12 carbons (an alkyl chain) at the 5' end as illustrated in FIG. 3. Other modified linker arms, for example but not limited to PEG oligomers, and poly T as illustrated in FIG. 3 could also be used to bond the functional group to the coating. In FIG. 3, the number of repeat groups in the linker can vary with m ranging from about 1 to about 3, n ranging from about 6 to about 12, and p ranging from about 1 to about 4, however other values of m, n, and p are possible. Reactive functionalities on the linkers may include but are not limited to amine, thiol, hydroxyl, carboxylic acid or other groups for linking to the imidazole coating functional groups. Other nucleotide sequences can be used and the linker arm can include other flexible organic chains of varying size. In some embodiments the telomerase primer includes from about 12 to about 30 bases, in other embodiments the telomerase primer includes from about 18 to 26 bases. Non-limiting example of functional groups and linkers are shown in FIG. 3.

A UV absorbance method can be used to confirm the success of the linking reaction and to measure the number of linked DNA strands or other functional group per fluorescent nanocrystal particle. These particles may be washed by centrifugal filtration (tangential flow filtration, Millipore, 10 kD), and the concentration of the DNA-FNCs conjugate, or other functional group bound to a coating on the fluorescent nanocrystal, adjusted to the concentration of a known standard solution of FNCs (control). The UV absorbance (OD) difference at an absorption wavelength between the functional group bound FNC, for example the 260 nm absorption between the DNA-FNCs conjugate and the control, can be attributed to the linked functional group. Depending upon the number of OD units per functional group, in the case of the DNA functional group each OD unit represents ~25 µg/ml oligonucleotides, the number of functional groups on the coated fluorescent nanocrystals can be determined. In the case of the DNA functional group, calculations indicated that about 170 nucleic acid units were linked to each particle of FNCs. The linking and characterization of surface loading other functional groups can be made in a similar fashion.

Figure 4:
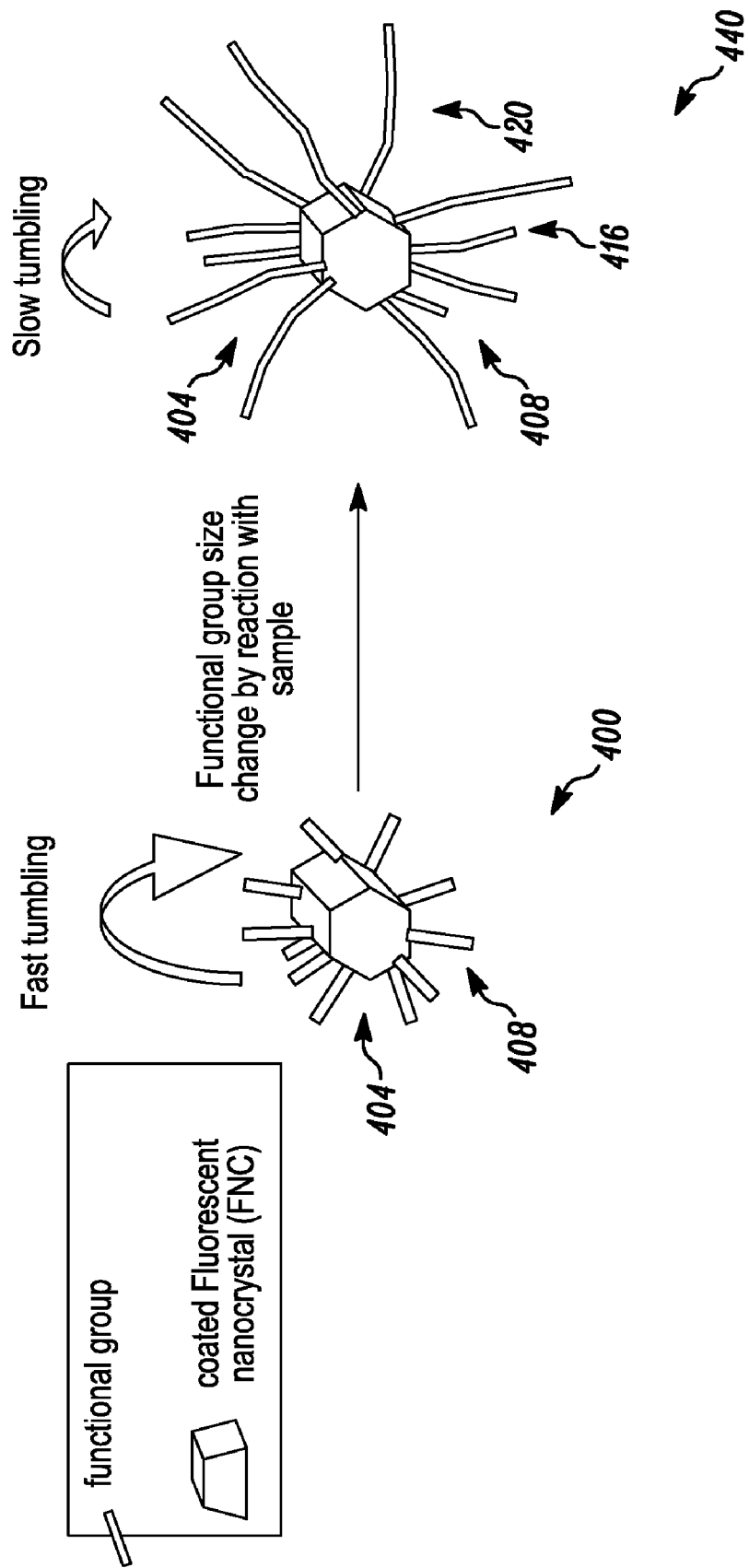
FIG. 4 illustrates bonding one or more functional groups to coated fluorescent nanocrystals and that reaction of the one or more functional groups with a target molecule in a sample can sequentially modify or grow the size or mass of one or more of the functional groups to change a spectral property and or a physical property (tumbling or mobility) of the functionalized nanocrystal.

Telomerase is relatively insensitive to steric hindrance and able to extend the 3' ends of DNA substrates attached to solid surface through the 5' end as illustrated in FIG. 4. Phosphothiolate-modified oligonucleotide primers can be used to increase both the affinity and velocity of elongation by telomerase. Telomerase substrate sequences with and without phosphothiolate modification can be linked to the thermally stable and water soluble imidazole group bound coated fluorescent nanocrystals.

Telomerase primers or other functional groups can be coupled to imidazole bound coated FNCs in several different wavelengths (520, 560, and 600 nm). Other coatings which provide a quantum yield of 70% or more, fluorescent thermal stability above about 25° C., preferably above 37° C. may also have functional groups coupled to their coating. For example, one ml of 25 nM FNCs solution in conjugation buffer (50 mM MES, 200 mM NaCl, pH 6.5) can be treated with 3 mM EDC and 5 mM sulfo-NHS to activate surface carboxyl groups of the coating. Excess cross-linkers can be removed by dialysis (10 kD, Pierce) against the conjugation buffer. Activated FNCs can be reacted with different concentrations of 5' amine linker modified TS primers, for example but not limited to (1, 10, 20 µM of the modified primer in 1 ml PBS). The number of functional groups per FNC particle can be adjusted using for example reaction time, reaction temperature, functional group concentration, coating surface reactive group density, or any combination of these to achieve optimal surface functional group coverage. For example, the number of telomerase primer strands per FNC particle can be adjusted using for example reaction time, reaction temperature, and functional group concentration, to achieve the telomerase primer surface coverage for telomerase detection applications. The final FNCs-coating-TS conjugates can be purified and concentrated by using centrifugal filtration (Millipore, 10 kD). The number of TS strands conjugated per FNC particle can be measured using UV absorbance. To vary the surface density and or accessibility of functional groups to target molecules, a cellular substrate, or to other fluorphores, various length, branched, or heteroatom substituted linkers may be used for the bonding the functional groups to the coating. For example, to modify telomerase accessibility to a substrate, TS primers with various alkyl linker arms of from about 6 to about 12 carbons at the 5' end could be used.

Figure 7:
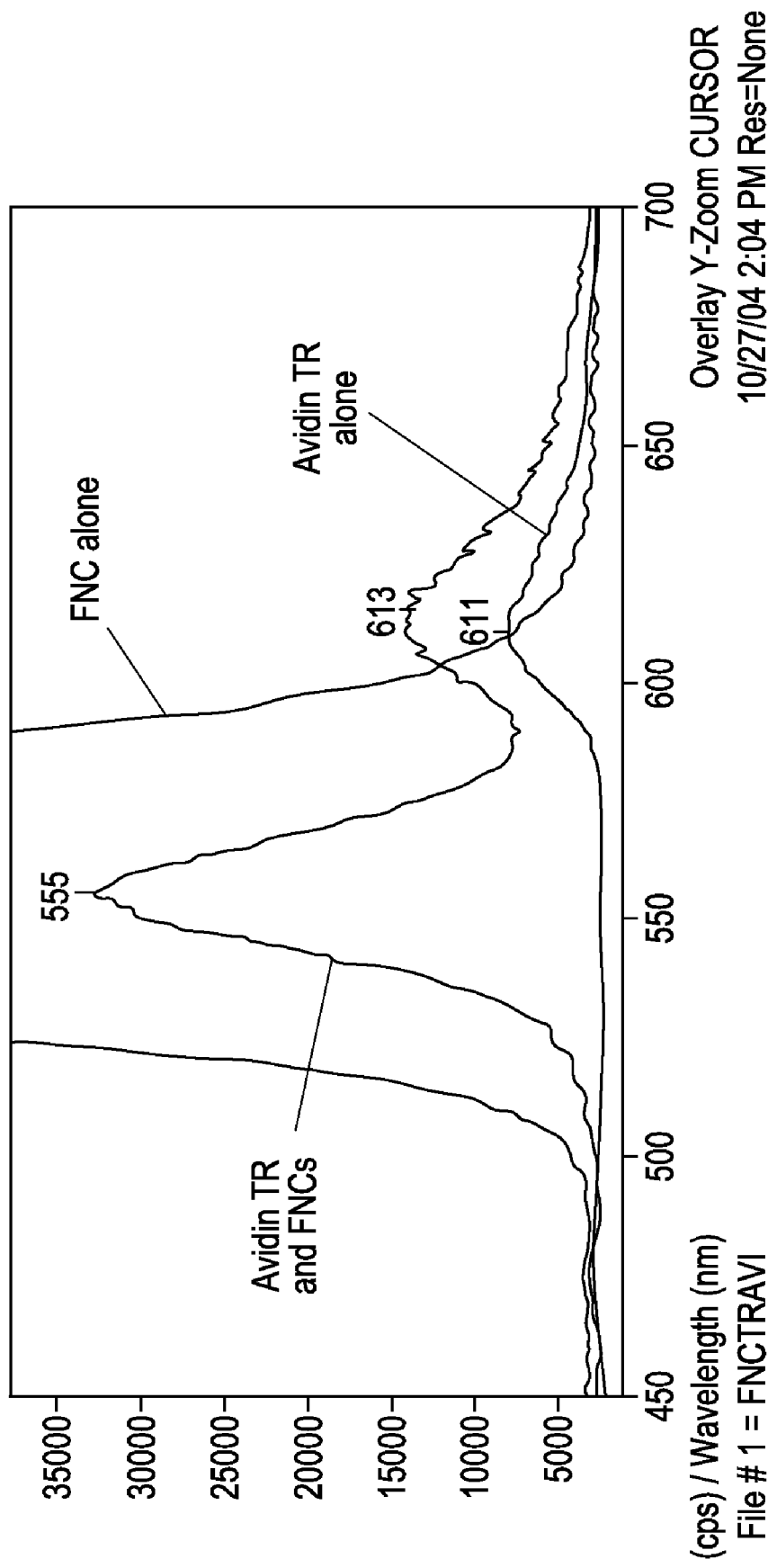
FIG. 7 Interaction between fluorescent nanocrystal and a fluorophore like Texas Red. Emission spectra of 30 μg/ml (500 nM) avidin-Texas Red (TR) alone or in the presence of 5 μg/ml (17 nM) fluorescent nanocrystals (555 nm emission). The strong cationic charge of avidin-TR caused strong association with fluorescent nanocrystal (negatively charged). All solutions were excited at 410 nm.
Figure 8A:
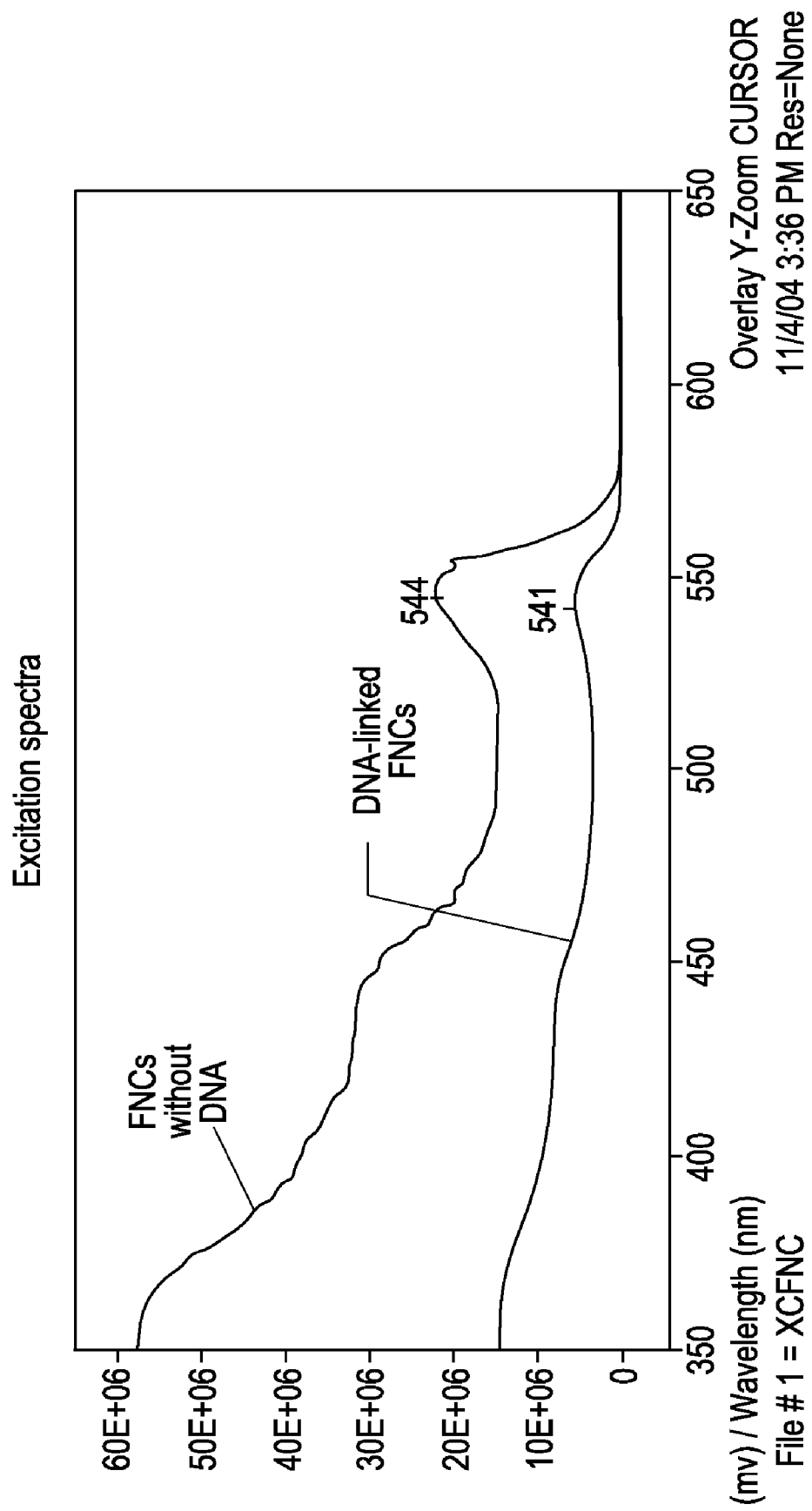
FIG. 8A illustrates DNA linking effect on the excitation spectral properties of fluorescent nanocrystals with (541 nm) and without (544 nm) DNA functional groups.
Figure 8B:
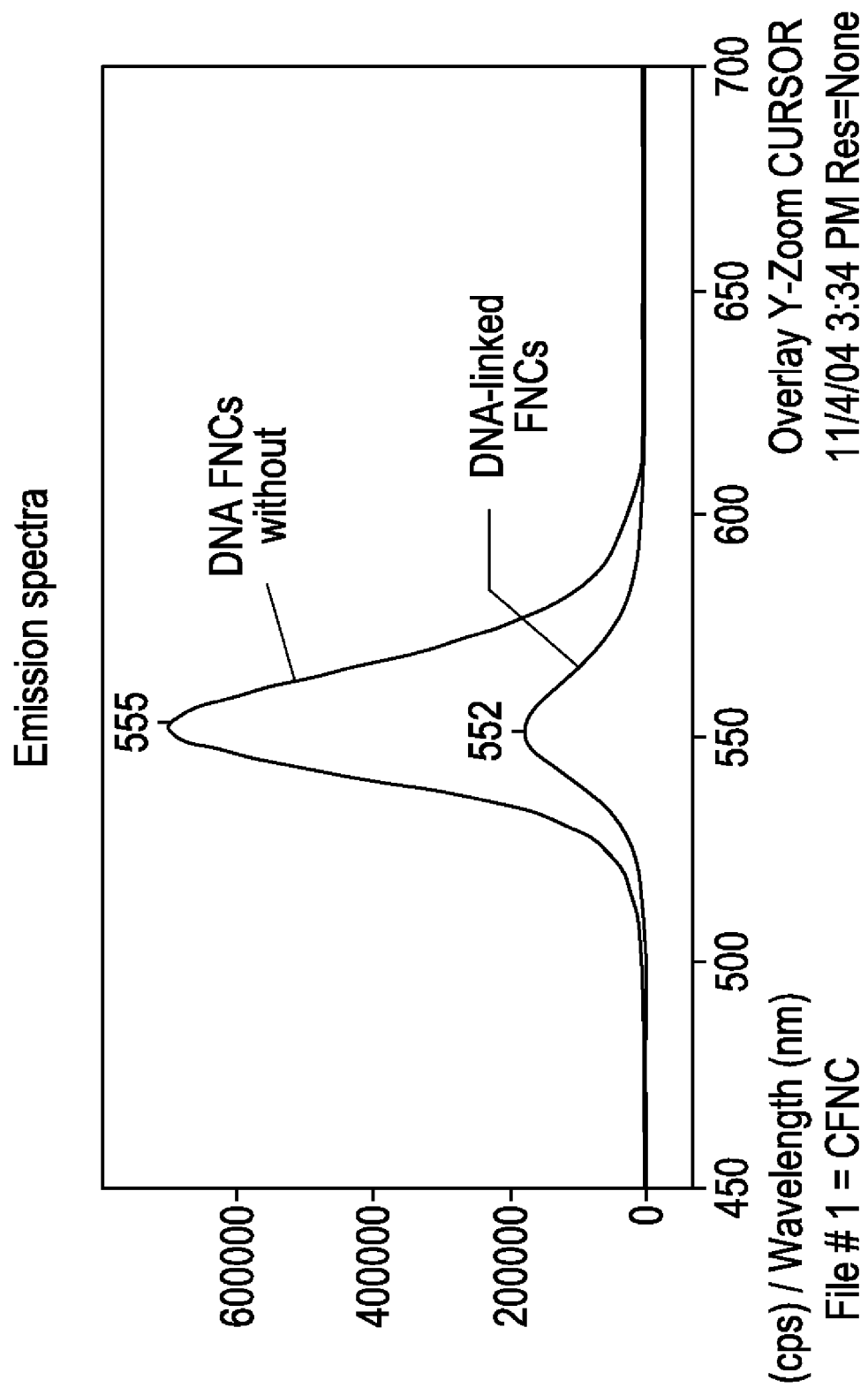
FIG. 8B shows an emission spectra with a peak at 555 nm without DNA functional groups and a peak at 552 nm with DNA functional groups linked to the fluorescent nanocrystal. It is expected additional changes in the spectral properties of the fluorescent nanocrystals with DNA bonded to the coating would occur with a change in the size of the bound DNA.

In some embodiments cadmium selenide core nanocrystals coated with a zinc sulfide inorganic shell to a specific size (color) and spectral characteristics can be synthesized using protocols based on thermolytic reactions of precursors in coordinating solvents. The core/shell nanocrystals are dissolved in a pyridine/chloroform solvent and can then be functionalized. The nanocrystals can be extracted by concentrated aqueous solutions of imidazole ligands. Following dialysis a thin layer or coating of imidazole ligands, where imidazole groups are bonded to the fluorescent nanocrystal, is formed on the surface of the fluorescent nanocrystal. The surface imidazole ligands can optionally be cross-linked. These imidazole coated FNCs can be washed with a suitable buffer using centrifugation filters, resulting in imidazole coated fluorescent nanocrystals configured with surface carboxyl groups available for covalent linking with various ligands such as telomerase primers or other functional groups. Due to electronic interactions, this coating process can produce enhancement in the fluorescence efficiency of CdSe nanocrystals and can produce an energy sensitization effect that makes such fluorescent nanocrystals highly responsive to surface changes. For example, the responsiveness of such fluorescent nanocrystals to surface interactions with DNA or with other fluorochromes was demonstrated in the results shown in FIG. 7, FIG. 8A and FIG. 8B. The spectra in FIG. 7, FIG. 8A and FIG. 8B show the intensity changes of FNCs emission after interaction with Texas Red or DNA, respectively.

In various embodiments, CdX core nanocrystals are coated with a higher bandgap inorganic shell and are further coated to permit bonding of one or more functional groups. In some embodiments the number of functional groups is greater than about 25 and preferably greater than about 100 functional groups bonded to the coating on the high bandgap surface of the shell. The coating on the inorganic shell results in fluorescent nanocrystals that are very stable in aqueous environments, and in some embodiments retain useful fluorescence when stored for about 24 days or longer at a temperature of at 45° C. or higher without light protection. Fluorescent nanocrystal having different fluorescent emission can be functionalized. In one embodiment, the coating on the fluorescent nanocrystals is functionalized with short strands of telomerase substrate DNA (TS). If telomerase activity is present in a sample, the sample may include nucleotides, acceptor derivatized nucleotides, donor derivatized nucleotides, cells or other excipients, the telomerase will elongate one or more of the TS primer strands on the fluorescent nanocrystal. The elongated primers linked to the fluorescent nanocrystals can result in a change in the spectral and or physical properties, like tumbling or mobility, of the fluorescent nanocrystal.

The effect of additional molecules added or removed from the functional groups bound to the coating on the surface of a fluorescent nanocrystal on the spectral properties of fluorescent nanocrystals can be tested in a variety of ways. For example, water soluble and biologically compatible imidazole functionalized nanocrystals having telomerase substrate primer strands bonded to the nanocrystals may be tested using cancer cell lysate specimens with known telomerase activity. The telomerase present in the cancer cells can elongate the telomerase primer strands in the presence of dNTPs and change the spectral properties of the FNCs as dNTP molecules are added to the functional groups bound to the coating of the FNCs. The change in spectral properties can be recorded for example, but is not limited to, a change in the Stokes shift, a change in polarization/anisotropy, as well as energy transfer between FNCs and matching fluorescent molecules (FRET). The change in spectral properties of FNCs can be compared with and correlated to a traditional TRAP assay for the detection of telomerase activity.

Besides dNTP's, a variety of other molecules of an organic or inorganic nature may be added sequentially to the functional groups bound to the coating on the surface of fluorescent nanocrystals to detectably change the optical and or physical properties of the FNCs. The molecules added to the surface of the nanocrystals or to reactive functionalities of a coating on the surface of the nanocrystals, and preferably a coating with imidazole groups bound to the fluorescent nanocrystal, may include, but are not limited to organosilanes, nucleotides, amino acids, polypeptides, nucleic acids, glycoproteins, eukaryotic cells, prokaryotic cells, lipoproteins, a substrate, and the like. The molecules may be in vivo, in vitro, in situ, or ex vivo.

Changes in the size or mass of one or more functional groups bonded to coated fluorescent nanocrystals upon reaction with one or more target molecules can be used to detect target molecules in a sample. The reaction of the functional groups with the target molecules may result in a change in the size or mass of the functional groups as molecules in the sample, which may be the same or different from the target molecule, are sequentially added or removed from one or more of the functional groups. The addition of dNTP's to DNA primer strands bonded to a coated fluorescent nanocrystal is a non-limiting example of the sequential addition of multiple dNTP molecules to the coated fluorescent nanocrystals that results in a change or growth in the size or mass of the functional groups in the coating. The addition of dNTP's to these primer strands in the presence of a target molecule like a reverse transcriptase, such as teleomerase, is a non-limiting example of molecules different from the target molecule that can add to the functional groups in a sequential manner. Alternatively, portions or all of the functional group may be sequentially removed by reaction with a target molecule in a sample. The removal of multiple amino acids from a bound peptide functional group or the cleavage of a functional group containing a lactamase sensitive bond are non-limiting examples where the sequential removal or degradation of a portion of a functional group can be used to modify the size, mass, or presence of fluorphores from the functional groups.

Spectral property changes related to changes in the length or mass of functional groups bonded to the coating upon reaction with a target molecule in a sample can be verified for example using cancer cell lysate specimens. Changes in the spectral properties can be recorded based on Stokes shift, polarization/anisotropy, as well as energy transfer between FNCs and matching fluorescent molecules (FRET). A spectral change related to a change in the size or mass of functional groups bonded to the coating upon reaction with a target molecule in a sample can be correlated to results from a traditional TRAP assay for the detection of telomerase activity in the cancer cell lysate specimens.

Fluorescent nanocrystals with functional group like telomerase primers can be used to detect telomerase activity in human tumor specimens from biopsies, fine needle aspirates, washings, brushings, etc. Testing for example can be conducted on malignant glioma specimens or other tumor types. Detection platforms that involve real time imaging in live cells, microscopic imaging on histology sections, high throughput formats, and lateral flow strip assay systems can also be used.

A composition that can be used to detect a target molecule like telomerase in a sample can be constructed by conjugating short strands of telomerase substrate DNA to fluorescent nanocrystals of specific spectral characteristics. It is advantageous for increased sensitivity to conjugate or bond functional groups like telomerase primers to a coating on the fluorescent nanocrystals that provides high numbers of functional groups on the fluorescent nanocrystal, for example greater than about 25, or greater than about 100. It is advantageous to have fluorescent nanocrystals that are stable at elevated temperatures. For example, elevated temperatures can be used for direct incubation of fluorescent nanocrystals with cells, to modify the reaction conditions for bonding functional groups to a coating on the fluorescent nanocrystals, or for other purposes. In embodiments of compositions, the coated fluorescent nanocrystals or coated fluorescent nanocrystals with functional groups bound to the coating are stable and retain useful fluorescence for target molecule detection at temperatures of about 20° C. or greater, at temperatures of about 25° C. or greater, at temperatures of about 37° C., or temperatures of about 45° C. or greater. It is advantageous for detection sensitivity to conjugate or bond functional groups like telomerase primers to a coating on the fluorescent nanocrystals that have a quantum yield of about 70% or greater. In the case of a functional group like telomerase primers linked to imidazole bound coated fluorescent nanocrystals, telomerase activity in a sample in the presence of dNTP's, (for example a mixture of dATP, dCTP, dGTP, and a fluophore or acceptor like Texas-Red 14-dUTP) can elongate the functional group telomerase substrate primer strands, causing a change in the size, mass, and spectral properties of the linked fluorescent nanocrystals. Changes in the spectral properties can be detected using simple cuvette assay platforms for fluorometry, polarization/anisotropy, and/or microscopy. Detection can also include simple lateral flow techniques (for on site diagnostic use in small clinics, doctor's offices, etc.), real time detection and monitoring in living cells, and high throughput formats.

Various combinations of high surface coverage of functional groups, temperature and fluoresce stability, or high quantum yield of the coated fluorescent nanocrystals may be used to detect a wide variety of target molecules that react with one or more of the functional groups bonded to the coating to change their size or mass. Changes in the surface coverage of functional groups, quantum yield, temperature and fluorescence stability of the functionalized fluorescent nanocrystals can be made by modifying the number and type of surface groups in the coating.

For target molecules that act as a marker for a condition, for example an enzyme like telomerase which acts as a marker for a majority of cancers, fluorescent nanocrystal based sensing utilizing functional groups bonded to a coating can be adapted for use in applications that involve large population screening, anticancer drug discovery and therapeutic drug monitoring.

Changes in the size or mass of functional groups bonded to the coating on the fluorescent nanocrystals can be detected through changes in the spectral properties of the functionalized nanocrystals. For example, as illustrated in FIG. 4, the detection of a target molecule in a sample can be determined by reaction of functional groups 408 bonded to a coated fluorescent nanocrystal 404. The coating can include imidazole containing molecules bonded by an imidazole group to the fluorescent nanocrystal. Reaction of the functional groups 408 with the sample may result in elongation of the one or more of the functional groups as illustrated for 416 and 420. The change in the size of the functional groups 408 can result in a difference in the spectral properties of the coated fluorescent nanocrystal with functional groups 400 compared to the spectral properties of the coated fluorescent nanocrystal with modified functional groups 440. In one embodiment, telomerase detection can be derived from thermally stable coated functionalized fluorescent nanocrystals as illustrated in FIG. 4. Short strands of telomerase substrate DNA (TS), illustrated by functional group 408, can be linked to imidazole bound coating on fluorescent nanocrystals (FNCs) 404. If telomerase activity is present in a sample, the DNA strands 404 can become elongated, illustrated by 416 and 420, in the presence of dNTP's in the sample, producing a change in the spectral properties of the FNCs from 400 to 440.

The effectiveness of thermally stable functionalized fluorescent nanocrystals for the detection of telomerase activity in cancer cell lysates can be demonstrated using established cell lines with confirmed telomerase activity such as U373-MG and U251-MG cells, and HCT-116 colon. Normal human fibroblasts (MRCS and WI38) can be used as a negative control, and SUSM-1 and Saos-2 osteosarcoma cells which possess alternative lengthening of telomeres. CHAPS cellular lysates of various protein concentrations can be incubated with telomerase functionalized coated fluorescent nanocrystals (FNCs-TS) in a telomerase incubation buffer at or about 37° C. Samples with dNTP's, matching dNTP-acceptors, or a combination of these and having telomerase activity will elongate the TS primers bonded to the coating on the FNCs surface, producing a change in their spectral characteristics. Spectral signals related to the change can be recorded by one or more of fluorescence polarization, Stokes shift, fluorescence resonance energy transfer.

Figure 5:
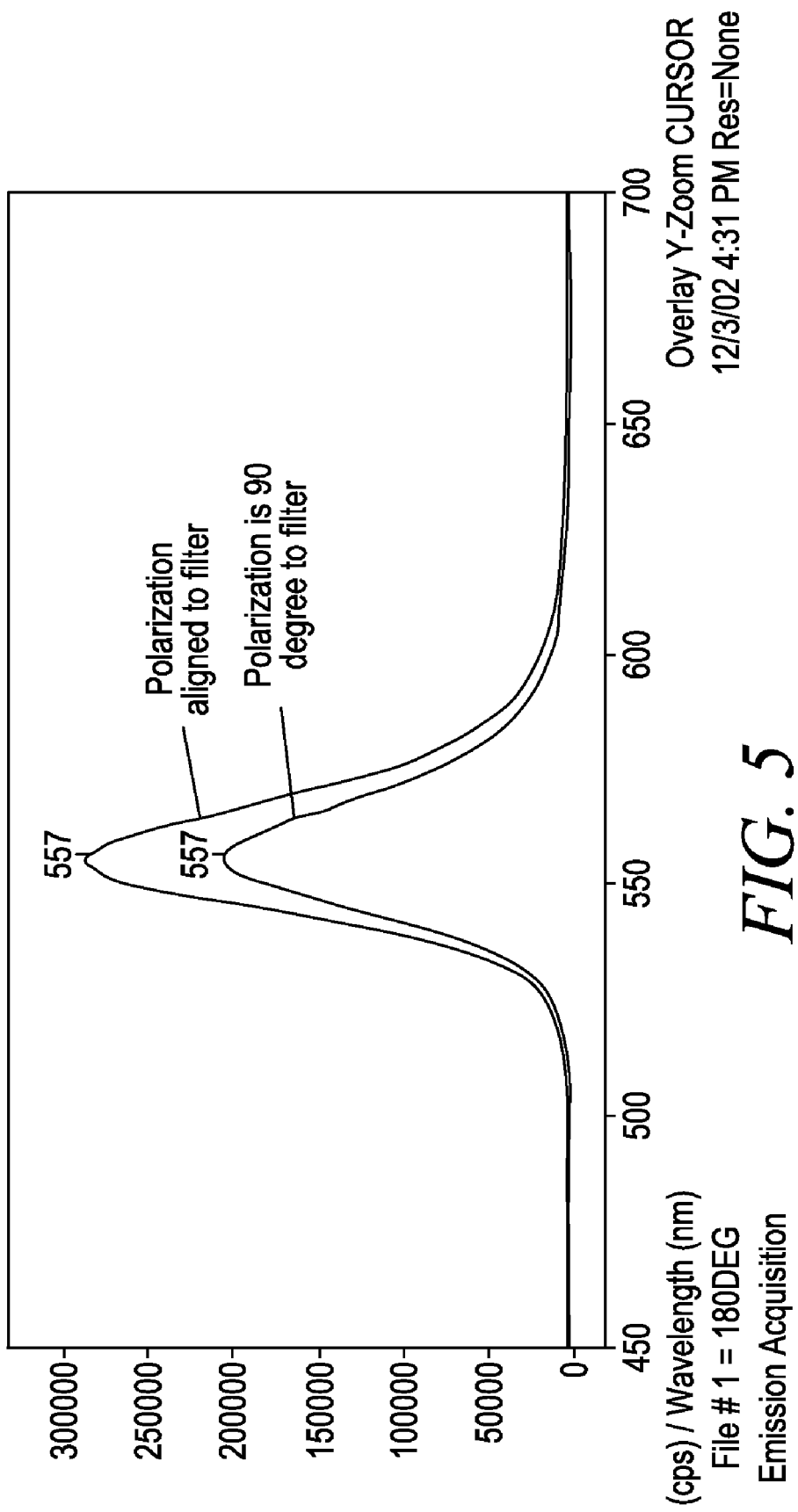
FIG. 5 The tumbling of fluorescent nanocrystal depolarizes polarized light. A fluorescent nanocrystal solution was analyzed using linear polarizers with 99.5% efficiency (Kenko PL46 mm). A solution of fluorescent nanocrystals (250 nM in borate buffer) was excited by polarized light and the fluorescent nanocrystals emitted depolarized light at 557 nm as evidenced by the limited quenching of a 90-degree polarization filters.

Signal detection based on fluorescence polarization (FP). If polarized light is used to excite a solution of FNCs, a portion of the emitted light will be depolarized due to the rapid "tumbling" of the FNCs in solution (enabled by their nanometric size). Changing the size of the surface bound ligands, for example elongating the TS strands on the surface of FNCs by telomerase as illustrated in FIG. 4, can induce a change in the degree of tumbling (i.e., depolarization). This alteration is proportional to the activity level of a target molecule in a sample like telomerase. The signal can be recorded by a fluorometer equipped with a polarization module. Changes in the size or mass of functional groups bonded to the coated fluorescent nanocrystals may be detected based on Fluorescence Polarization (FP). When depolarized light is used to excite a solution of FNCs, a portion of the emitted light will be depolarized due to the rapid "tumbling" of the FNCs in solution (enabled by their nanometric size). It is possible to measure molecular weight changes in CdS nanocrystals linked to peptides using FP analyses. It is reasonable to expect that molecular weight changes occurring from changes in the size or mass of functional groups bonded to the imidazole coated fluorescent nanocrystals can also be made. An example of the applicability of FP on FNCs is shown in FIG. 5.

Fluorescence polarization (FP) is a relative value that can be expressed as:

$$FP = \left(\frac{F_{para} - P_{perp}}{F_{para} + F_{perp}}\right)$$

where $F_{para}$ is the fluorescence intensity parallel to the excitation plane; and $F_{perp}$ is the fluorescence intensity perpendicular to the excitation plane. The correlation between FP and molecular mobility (i.e., molecular weight) can be described by Perrin equation:

$$\left(\frac{1}{FP} - \frac{1}{3}\right) = \left(\frac{1}{FP_o} - \frac{1}{3}\right) \times \left(1 + \frac{\tau}{\phi}\right)$$

where $FP_o$ is the fundamental polarization of the fluorophore, $\tau$ is the excited state lifetime and $\phi$ is the rotational correlation time. The rotational correlation time $\phi$ is dependent on the effective molecular volume of the fluorophore, solvent viscosity and temperature. Advantageously, the high temperature stability of the coated fluorescent nanocrystals with imidazole group bonded to the nanocrystal permits a wide range of temperatures and solvent viscosities to be used for detection of changes in fluorescence polarization due to changes in mass or size of functional groups bound to the coating.

In some embodiments utilizing the coating with imidazole molecules bonded by an imidazole group to the fluorescent nanocrystal, experimental results have shown that each coated FNC particle can be linked to about 170 strands of DNA telomerase primer. A typical cancer cell extract (e.g., $10^4$ HeLa cells) can produce telomeric DNA elongation of 300-1000 base units within 1 hr reaction time. Based on the possible number of linked TS strands per FNC particle and the processivity of telomerase, elongated TS strands can induce a large increase in the effective molecular weight and degree of tumbling (i.e., depolarization). For example, assuming that the number of linked TS strands is about 100 per particle and only 10 strands are extended an average of 500 base units each by telomerase, the increase in the effective molecular weight of a yellow FNC (MW ~300 kD) would be equal to about: 10 (n strands)×500 (n base units)×300 (average base unit MW)=$1.5 \times 10^6$ D which is approximately a 5-fold mass increase. The excited state lifetime of FNCs was found to be from about 8 ns to about 12 ns. For aqueous solutions of proteins, the value was found to increase by about 1 nanosecond per 2.4 kD increase of molecular weight. This indicates that about (2.4 kD×10 ns=24 kD) or about 80 base units per particle could be used to induce alteration in the polarization of FNCs. Consequently, changes in the size or mass of functional groups linked to coated fluorescent nanocrystals or imidazole bound coated fluorescent nanocrystals, similar to the telomerase-induced alteration in molecular weight, would be sufficient to cause tumbling changes that are proportional to the activity of a target molecule in a sample such as a telomerase. The signal can be recorded by a fluorometer equipped with a polarization module (e.g., Fluoromax-3). Instrumentation that can provides precise measurement of FP with less than ±0.2% margin of error or better may be used.

Signal detection based on fluorescence resonance energy transfer (FRET). Energy transfer or exchange can be achieved by the direct resonance interaction of donor and acceptor pairs of molecules. In this case, FNCs can play the role of donor or acceptor. It has been shown that telomerase is able to use dye-labeled nucleotides to extend the telomeric DNA. Using nucleotides labeled with a FRET matching ligand, telomerase's extended strands will interact with the FNCs inducing a FRET effect. The degree of FRET interaction is directly correlated with the amount of telomerase activity. Another FRET approach involves hybridization of the extended strands with a complementary oligonucleotide labeled with a matching FRET ligand. This matching FRET ligand can accommodate different color FNCs or standard organic fluorophores. The use of FNCs in FRET applications may be particularly advantageous because of the high emission intensity of the coated fluorescent nanocrystals of the present invention, and because of their long fluorescence lifetime (about 50 ns, which is an order of magnitude more than conventional fluorochromes). Consequently, background fluorescence sources (e.g., autofluorescence) with shorter lifetimes than FNCs can be gated out by the detector, resulting in a higher signal to noise ratio. Changes in the size or mass of functional groups bonded to the imidazole bound coated fluorescent nanocrystals may be detected based on Fluorescence Resonance Energy Transfer (FRET). Fluorescent nanocrystals are able to participate in resonance energy transfer or exchange processes analogous to FRET. The broad excitation spectrum, ability to make a variety of sizes of coated fluorescent nanocrystals provides great flexibility in the selection of suitable donor/acceptor pairs. The high quantum yield (70% or more), high surface coverage or density of functional groups provided by the coating provides for improved detection sensitivity. The thermal stability of the coated fluorescent nanocrystals enable them be used in FRET applications at temperatures above 20° C., and preferably above 37° C., allowing them to be used at high temperatures during such processes as incubation with samples, incubation with samples including cells, or in kinetic studies. The use of these FNCs in FRET applications is advantageous due to their high emission intensity and their long fluorescence lifetime (about 10 ns) thereby enabling background fluorescence sources with shorter lifetimes to be gated out by the detector, resulting in a higher signal to noise ratio.

Figure 6:
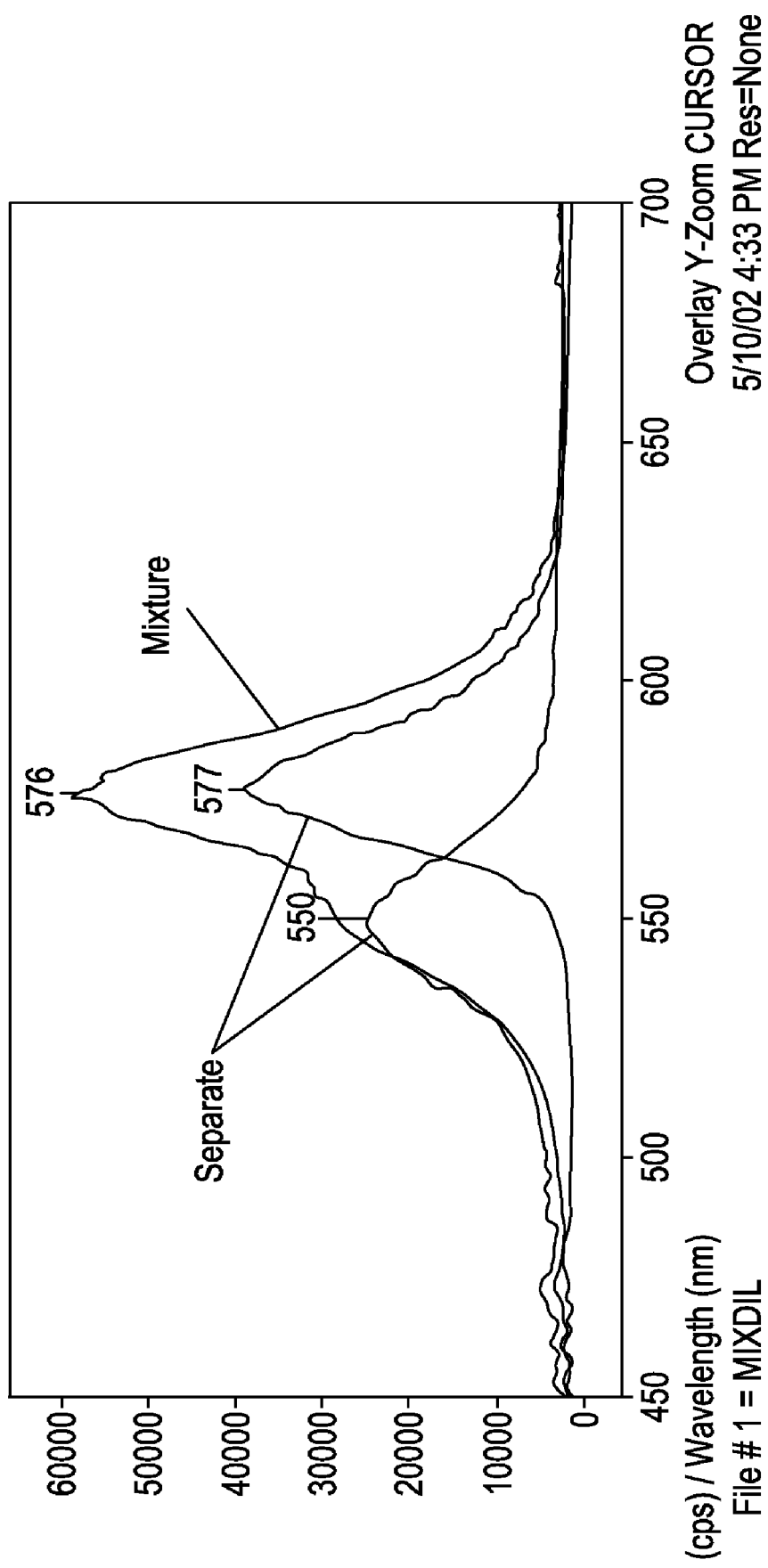
FIG. 6 Interaction between two types of fluorescent nanocrystal (550 nm and 577 nm emission). Emission spectra of 10 μg/ml of each type of fluorescent nanocrystal were measured separately or dissolved in the same solution. All solutions were excited at 410 nm.

Utilizing a coating material with imidazole-containing molecules bonded by an imidazole group of the molecule to the surface of the fluorescent nanocrystals, the ability of such FNCs to interact with other FNCs FIG. 6, or with conventional fluorochromes FIG. 7 through FRET-like processes is shown. In FIG. 7, Avidin-Texas Red (TR) had the function of acceptor and showed strong FRET-like interaction with FNCs (donor) due to its cationic charge and ability to bind to the negative surface of these or similar coated FNCs. The strong association between FNCs and Avidin TR was confirmed by the ability of Avidin TR to sediment with FNCs after centrifugation.

Telomerase is able to extend the telomeric DNA using dye-labeled nucleotides. Using nucleotides labeled with a FRET matching ligand, extended strands can interact with FNCs, inducing a FRET effect directly correlated with the amount of telomerase activity. Advantageously, the coated fluorescent nanocrystals in embodiments of the present invention do not utilize a thiol linking protocol to bind telomerase primers to the fluorescent nanocrystal or to an imidazole bound coating on the fluorescent nanocrystal. The greater stability of the present coating provides stability necessary to perform analysis of telomerase under a variety of conditions including incubation with cells at physiological temperatures of about 37° C. or more. Their high quantum yield and or high number of functional groups that can be bound to the coating can provide greater detection sensitivity. By monitoring the quenching of the donor fluorescence (i.e., FNCs) or the enhancement of the acceptor emission (i.e., fluorophore), quantitative determination of telomerase activity can be achieved with these imidazole coated fluorescent nanocrystals. Average telomerase activity can add about 5000 base units (in the form of TTAGGG repeats) per particle. Assuming that a TR-labeled thymidine base (T) is used in the assay, then the average telomerase activity could result in the incorporation of about 1600 TR molecules per particle. The experiment for FIG. 7 exhibited strong FNC quenching at an acceptor/donor molar ratio of only about 30 (500 nM Avidin TR/17 nM FNC), far less than the achievable acceptor/donor average ratio of about 1600. This indicates that these coatings with bonded functional groups can provide high sensitivity in FRET-based detection methods.

Figure 2:
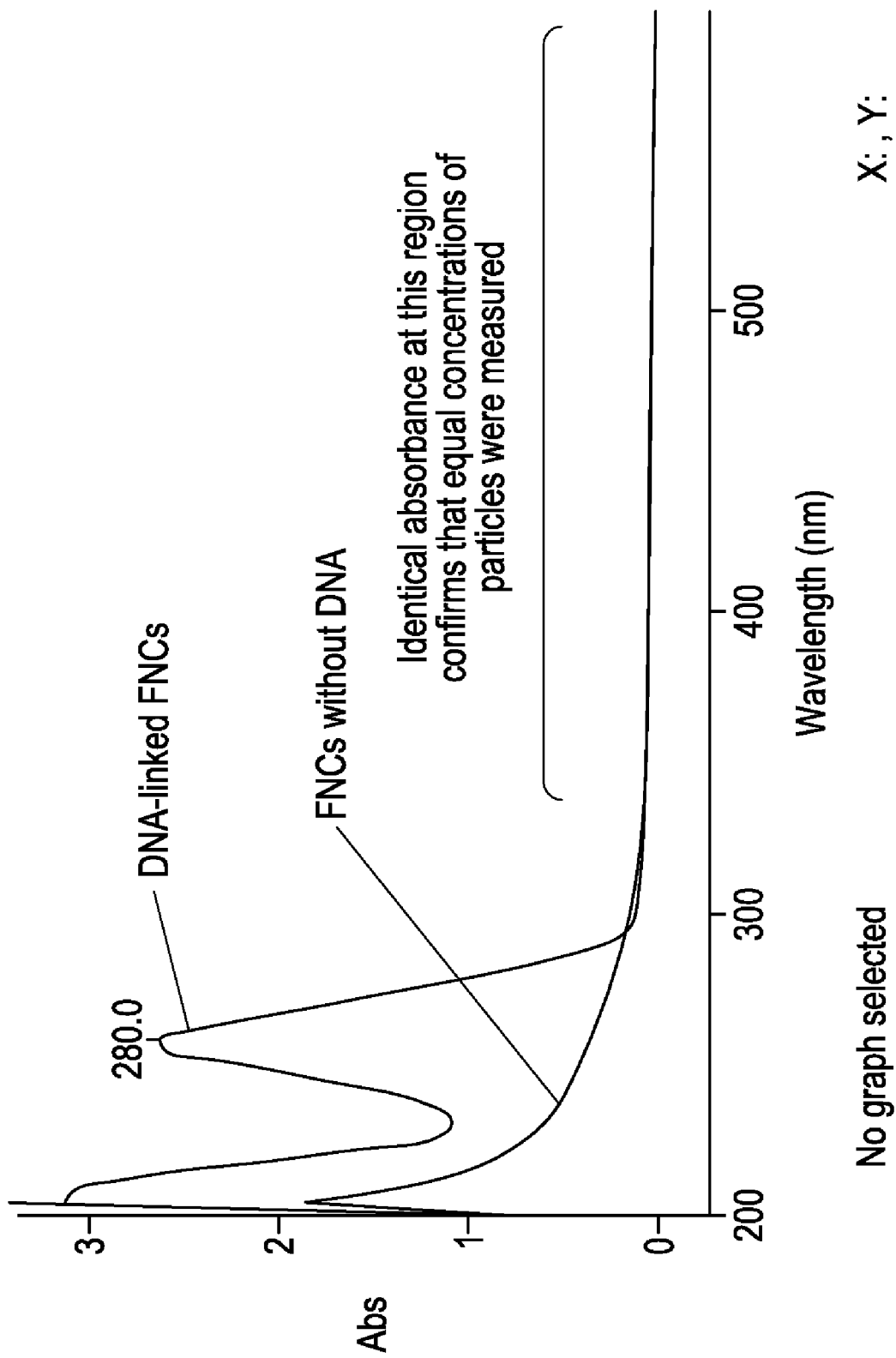
FIG. 2 Illustrates the absorption spectrum of fluorescent nanocrystals and fluorescent nanocrystals bonded to DNA.

Signal detection based on Stokes shift. Due to the fact that FNCs are very small particles with high surface to core ratios, their electronic properties can be highly sensitive to surface interactions with ligands and functional groups bonded to coatings on their surface. For example, DNA strands absorb UV at 260 nm. The resultant absorbance interacts with the corresponding absorbance of FNCs, causing a shift (Stokes) in the amount and intensity of the spectral energy emission of the latter. As the short TS primers on the surface of FNCs are elongated by telomerase, the newly incorporated DNA may cause a chromatic shift directly proportional to the activity of telomerase. This chromatic shift can be recorded by a fluorometer. Sequential changes in the size or mass of functional groups bonded to the coated fluorescent nanocrystals may be detected based on Stokes Shift. The imidazole coating with imidazole groups bonded to the surface of the FNCs can enhance their responsiveness to energetic surface interactions. DNA strands absorb UV at 260 nm. As the short TS primers on the surface of FNCs are elongated by telomerase, the absorbance of the newly incorporated DNA interacts with the absorbance of FNCs, that can result in a change in the amount and intensity of the spectral energy emission of the latter. Linking even short oligonucleotides (26 base unit) results in chromatic shift and decrease in intensity (FIG. 2, FIG. 8A, and FIG. 8B). These findings are in good agreement with a recent study showing that DNA oligomers are able to induce concentration-dependent decreases in the emission intensity of CdS nanocrystals. Advantageously, the imidazole coated fluorescent nanocrystal can be used at temperatures above about 25° C. and can have high surface coverage of surface functional groups. Where the functional groups include telomerase primers, and based on the possible number of linked TS strands per FNC particle (e.g., about 170) and the processivity of telomerase (300-1000 base units per hour), telomerase activity can induce a large increase in the amount of DNA incorporated onto FNCs. This incorporated DNA can be effective in inducing significant spectral changes, which can be recorded by a fluorometer (e.g., the Fluoromax-3). A shift that may be attributed to a Stokes shift was observed in an experiment, results shown in FIG. 8A and FIG. 8B, which was about 3 nm for the amount of linked DNA.

FNCs may be used to detect telomerase activity in human tumor specimens from biopsies, fine needle aspirates, washings, brushings, etc. In some embodiments, the fluorescent nanocrystals are coated with an imidazole coating bound by imidazole groups to the fluorescent nanocrystal and where functional groups, like telomerase, are bound to reactive functionalities in the coating. Testing may be conducted on malignant glioma specimens and may also include evaluations with other tumor types. Detection platforms may include but are not limited to real time imaging in live cells, microscopic imaging on histology sections, high throughput formats, and lateral flow strip assay systems.

Analysis of telomerase activity on living cells. In living cells, the transfer of coated fluorescent nanocrystals (FNCs) with bound functional groups, such as telomerase conjugated to the imidazole coated FNC, may be introduced into the cytosol/nucleus by lipofection (making use of the DNA shell of the nanoprobes). Additionally, other commercially available DNA/protein transduction reagents (like BioPorter) can be used for an efficient but gentle transduction of the FNCs into living cells. Techniques to manipulate the physical properties of coated FNCs with bound functional groups (i.e., polarity and electrostatic interactions) can also be used to enhance cellular permeability. Standard, PEGylated or lipid-modified FNCs can be evaluated for cell permeability using typical cancer cell lines (e.g., HCT-116 colon carcinoma) with confirmed telomerase activity. Standard transfection reagents (liposomes and cationic lipids) can also be used for intracellular delivery of such FNCs. Transient and mild poration methods such as enzymatic poration with Streptolysin O, or standard electroporation may be used to enhance the cellular uptake of coated FNCs with one or more bound functional groups. Epifluorescence and confocal microscope images of these FNCs can be used to determine the location and internalization of functionalized coated fluorescent nanocrystals in live cells. Fluorescent signals at depth levels between about 1.5 and about 3.5 μm indicate the internalization of these delivered FNCs to cells. Telomerase activity is localized in both the cytosol and nuclei of cancer cells and internalized FNC-imidazole coated-TS particles would be accessible to telomerase regardless of their sub-cellular distribution.

For biological applications the fluorescent semiconductor nanocrystals are preferably water soluble. For example, cadmium selenide core nanocrystals may be coated with a zinc sulfide inorganic shell and can further be biologically functionalized. The functionalization step results in organically coated nanocrystals that are water soluble and biologically useful (compatible, may bind or react with molecules, polypeptides, or polynucleotides of interest). For example, to detect telomerase activity using fluorescent nanocrystals, the fluorescent nanocrystals can involve the conjugation of one or more short strands, from about 12 bases to about 30 bases, preferably about 18 to 26 bases, of telomerase substrate DNA (TS) to a water soluble, imidazole bound coating on the FNCs that are of specific spectral characteristics. If telomerase activity is present, it will elongate one or more of the TS primer strands linked to these water soluble fluorescent nanocrystals, resulting in a change in the spectral properties of the linked nanocrystal.

Where biological molecules are added to lengthen functionalities bonded to the surface of fluorescent nanocrystals, or where the biological molecules result in shortening of functionalities bonded to surface of the fluorescent nanocrystal, the biological molecules may be taken from a variety of sources and biological samples, which can include but is not limited to cell lysates, bodily fluids, tissue extracts, tissue sections. Alternatively the samples and spectral analysis/detection may be performed in real time on living cells.

To determine the telomerase activity in human tumor and normal cells, 10 tumor cell lines of various origins (human malignant glioma U373-MG and U251-MG cells, human malignant melanoma A375 and SK-MEL2 cells, human cervical cancer HeLa cells, human breast cancer MDA468 and T47D cells, human prostate cancer PC3 and DU145 cells, human renal cancer RCC cells) and 2 human fibroblasts (MRCS and WI38) can be selected and the TRAP assay performed. Telomerase activity was demonstrated in all tumor cells tested. In contrast, two fibroblast cell lines did not express detectable activity of telomerase. These tumor and normal cells may be used as controls and as a source of telomerase for comparison to changes in spectral properties or changes in mobility produced by the reaction of telomerase primers bonded to imidazole coated fluorescent nanocrystals with telomerase and nucleotides in a sample.

The elongation or shortening of one or more functional groups bonded to the surface of a fluorescent nanocrystal can be used in a sensor. For example, short strands, from about 12 bases to about 30 bases, preferably about 18 to 26 bases, of telomerase substrate DNA (TS) can be linked at the 5' end to water soluble and thermally stable coated nanocrystals (FNCs). If telomerase activity is present in a sample, the DNA strands will become elongated at the 3' end in the presence of added dNTP's, producing a change in the spectral properties of the FNCs. This kind of elongation of one or more bound functional groups 408 is illustrated in FIG. 4.

The fluorescent nanocrystals, which may be in a vessel, in a flow through system, aspirated, or on a substrate, can be contacted with the sample in a vessel. The temperature of the fluorescent nanocrystals and sample should promote reaction between the two where a target molecule is present. Preferably temperature does not degrade the nanocrystals or the target molecule and interfere with reaction. In some embodiments, the temperature can be between about 4° C. and about 50° C.

Selection of telomerase DNA substrate sequence (TS). The telomeric DNA sequence in humans consists of variable numbers of tandem repeats of simple G-rich sequences (TAGGGT)n, (SEQ ID NO:2), with a protruding G-rich overhang on the strand oriented 5' to 3' toward the chromossomal terminus. Telomerase is a ribonucleoprotein mainly composed of a catalytic protein subunit (TERT) with an RNA component that contains the templating domain. Using its RNA template, telomerase extends the G-rich ends of telomeres via a de novo process (i.e., without metabolic energy). Telomerase substrates can vary in length and sequence; the resultant enzyme affinity and processing velocity can vary. Phosphothiolate-modified oligonucleotide primers are an example of primers that can dramatically increase both the affinity and velocity of elongation of suitable primers by telomerase. Short telomeric sequences with and without phosphothiolate modification may bonded to imidazole coated fluorescent nanocrystals. Other substrate sequences such as but not limited to (5'-TTTTTTAATCCGTCGAGCA-GAGTT-3'), (SEQ ID NO:3), or those used in TRAP assay (5'-AATCCGTCGAGCAGAGTT-3'), (SEQ ID NO:4), or others can be bonded with a linker as illustrated in FIG. 3, to bond to the imidazole bound, imidazole coated fluorescent nanocrystals.

Generally fluorescent nanocrystal can be excited by a wavelength of light that is blue shifted from the fluorescent emission, and can be about 20 nm to about 30 nm shorter wavelength than the emission wavelength of the fluorescent nanocrystal. In some embodiments of the present invention excitation can be from about 300 nm to about 750 nm although other wavelengths are possible. Excitation sources suitable for characterizing the functionalized fluorescent nanocrystals of this invention include but are not limited to polychromatic ultraviolet and visible lamps, substantially monochromatic sources light, polarized light, beta emitters including but not limited to $^{33}P$, $^{125}I$, and $^3H$, or functional groups containing beta emitters (donors). Sources of light may include low, medium, and high pressure lamps as well as lasers. Electric current and electron bombardment of the nanocrystals may also me used for excitation. Suitable detectors may include but are not limited to visual detection, photodiodes, photomultipliers, heat detectors and charge coupled device detectors (CCDs); detectors may also include the use of polarizing filters.

The fluorescent nanocrystals with functional groups such as one or more telomerase substrate primer strands bonded to an imidazole coating can be tested using malignant glioma specimens taken for example from patient sample extracts (biopsies, fine needle aspirates, washings, brushings, etc). These nanocrystals can also be challenged with other types of tumors. Malignant gliomas are the most common primary tumors arising in human brain. A large majority of them are astrocytic tumors, which represent the largest tumor entity in the central nervous system. Gliomas are histologically classified into four grades (World Health Organization Grades I, II, III, and IV). Grades I and II indicate low-grade glioma, and Grades III (anaplastic astrocytoma, AA) and IV (glioblastoma multiforme, GBM) are malignant glioma. In Grade I or II gliomas, telomerase activity is detected in 0% or 0 to 33% of tumors examined (Grade I and II respectively). On the other hand, telomerase is expressed in the vast majority of malignant gliomas. GBM (Grade IV) can be used as patient samples. Tumor specimens can be obtained at the time of surgery from patients. Tumor tissues can be evaluated by a neuropathologist, and a small portion excised for pathological examination. Samples are preferably rapidly frozen and stored in liquid nitrogen. After pathological assessment, protein extracts can be prepared from approximately 100 mg of 20 frozen GBM tissues stored at −70° C. Aliquots of the extracts can be freshly frozen in liquid nitrogen and stored at −70° C. Protein concentration can be determined by the Bio-Rad Protein Assay (Richmond, Calif.).

Tumor tissues from other organs such as breast or prostate cancer collected, for example (26 tissues for each cancer) can be used to detect telomerase activity using telomerase functionalized imidazole coated fluorescent nanocrystals. Moreover, patient sample extracts obtained from fine needle aspiration biopsy (FNA) or brushing/washing can be tested. FNA is a safe, economical, and simple procedure for use in specific diagnoses and staging of various benign and malignant conditions of the uterus, ovaries, bladder, colon, pancreas, or liver. However, false negative rates are not low and the development of a new detection assay such as telomerase activity is needed. Twenty FNAs (from different sites and of different tumor types) of patients treated with a therapy can be collected. After processing for routine cytospin for pathological assessment, the remaining specimen from each case can be centrifuged at 7,500 g for 5 min and the cell pellet can be frozen and stored at −70° C. until used in the telomerase activity assay with the coated fluorescent nanocrystals. Brushing and washing techniques are routinely used for diagnosis of lung or cervical cancer. To analyze such specimens, (26 each) can be collected from patients with lung or cervical cancer and the samples prepared as described for FNA. Rapidly frozen clinical specimens from the Human Cooperative Tissue Network including advanced grades of human colon, head and neck, and/or ovarian tumors can be evaluated with telomerase primer functionalized imidazole coated fluorescent nanocrystals. Approximately 5 specimens of each type of tumor can be processed and examined following the protocols described.

Imaging studies may be performed on fixed or living cells, and on histology sections. A coated FNC-based telomerase activity assay that can include the monitoring of fluorescence signals in fixed or living cells, and on histology sections. Typically assays detecting telomerase activity in biological specimens (like TRAP: telomeric repeat amplification protocol; or an enzymatic assay) are based on heterogeneous cell or tissue extracts. This makes it difficult to distinguish telomerase positive from telomerase negative cells. The enzymatic activity of DNA polymerases as well as telomerase is preserved in snap-frozen tissue specimens and cell cultures. The telomerase activity will elongate the FNCs-coating-immobilized primers in situ, leading to a shift in the spectral properties. This can be visualized in a microscopic system. Using this in situ assay, it is possible to differentially determine telomerase activity of individual cells in culture, and from histology sections from cancer patients.

Confocal microscopy with spectral detection for imaging studies can be performed using confocal microscope such as a Zeiss ISM510Meta confocal microscope. This type of microscope provides for the visualization of multiplexed processes in biological specimens at a high spatial and temporal resolution combined with emission spectrum analysis. In addition to XYZ and the temporal dimension, spectral detection can be used to record spectral information (400-720 nm) of the fluorescence emitted by the specimen (5D analysis) treated with imidazole coated fluorescent nanocrystal having, for example functional groups capable of extension by telomerase. Reference spectra and a software implemented algorithms can be used to separate individual fluorescence signals from a multiplexed sample by linear unmixing.

Signal detection based on Stokes shift. The chromatic changes (intensity and Stokes shift) of imidazole bound imidazole coated fluorescent nanocrystal having for example functional groups capable of extension by telomerase, can be monitored and quantified at cellular resolution. The elongation of the FNC-immobilized telomere primers can induce a chromatic shift (Stokes shift) that can be proportional to the activity of telomerase in a sample. This spectral change can be monitored and quantified with cellular resolution. In microscopic analysis, linear unmixing can be used to discriminate between telomerase primer functionalized coated fluorescent nanocrystals elongated by telomerase and those that have not been elongated. The assay can be used to perform differential analysis on telomerase activity in individual cells. This in situ assay can be used to perform a differential analysis on telomerase activity in individual cells that have been treated with telomerase primer functionalized coated fluorescent nanocrystals.

Signal detection based on fluorescence resonance energy transfer (FRET). Using a microscope with a spectral detection mode it is possible to perform FRET experiments on biological samples like mammalian cells and tissue sections. A motorized scope (XYZ scanning table, laser excitation, filter switch, detector) and scripting language software can be used to automated sample analysis with a user defined selection of ROIs (region of interest). This apparatus permits an imaging sequence for the spectral and FRET analysis over a period of time at the chosen ROIs. With fluorescence labeling techniques, the telomerase activity can elongate coated FNC-immobilized telomerase primers in situ, leading to an incorporation of fluorophore-labeled dNTP into the primers. Under FRET conditions the high emission intensity of the FNCs is transferred to an acceptor fluorophore (dye-dNTP), resulting in an intense FRET signal which is proportional to the telomerase activity. FRET signals at various ROIs, time points, and samples can be used to quantify telomerase activity in situ.

Analysis of telomerase activity on fixed cells and histology sections. Due to the extremely high fluorescence intensity of the coated FNCs used to link with functional groups in various embodiments (U.S. Pat. Appl. Pub. No 20040009341 A1 and U.S. Pat. Appl. Pub. No 20030059635 A1 the contents of which are incorporated herein by reference in their entirety), assays such as the FNC-telomerase assay can be highly sensitive and enable a visualization of the enzymatic activity in situ and at cellular resolution. Additionally, the coated FNCs-based assay can be expanded by probing the biological samples with multiple other antigens (i.e. other tumor markers) using common fluorescence staining techniques. Making use of the linear unmixing procedure the multiplexed sample image can be separated into individual and quantifiable channels. Furthermore, tissue sections can be stained for common histo-pathological evaluation which offers a fast and comprehensive differential diagnosis of the tumor specimen by a pathologist. Such information can provide a high content analysis that may enable finger printing for an improved tumor classification.

Figure 9:
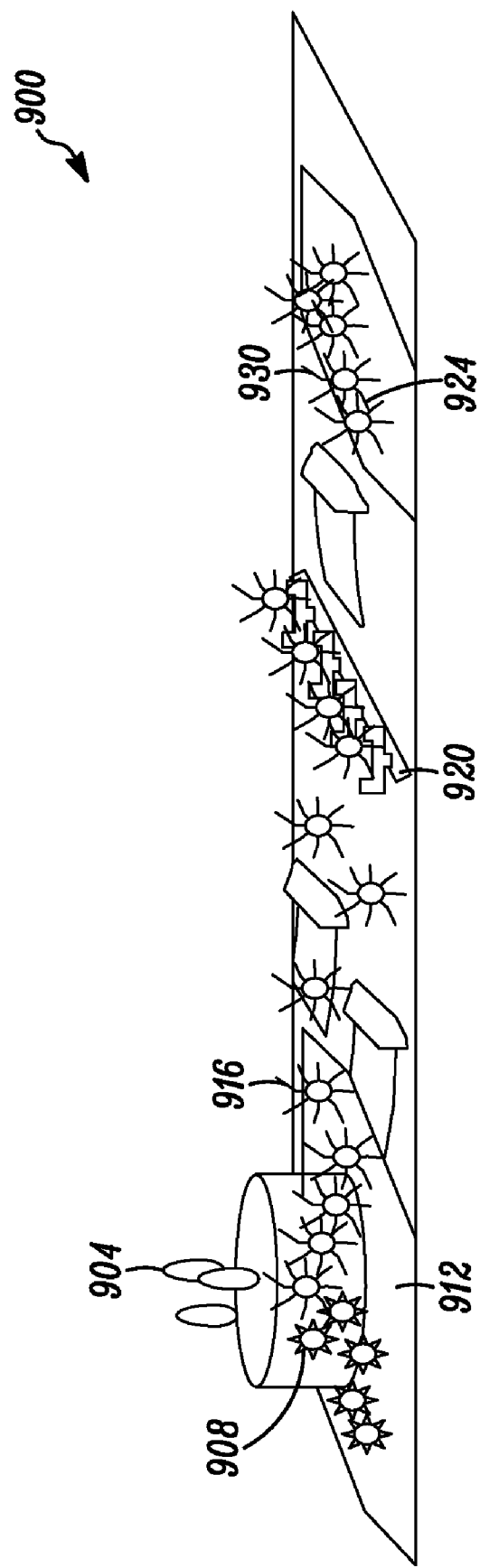
FIG. 9 illustrates a lateral flow assay to test a sample for one or more target molecules using fluorescent nanocrystals with functional groups that can have their size or mass modified by reaction in the presence of target molecule(s).

Lateral flow test strips may be used for qualitative or semi quantitative detection of many biological analytes. These devices generally include a substrate with a support pad and filtration medium located at one end of the substrate. The pad can be loaded with a reactive material, for example an imidazole coated fluorescent nanocrystal with one or more functional groups whose length can be changed by elongation or degradation by contact with a sample solution that can have a target molecule to be detected. When the target molecule is present, reaction between the material in the pad with the sample can change or modify the size of the fluorescent nanocrystal with one or more functional groups which can result in a difference in the rate of migration of the fluorescent nanocrystal with modified functional groups along the strip. The migrating fluorescent nanocrystal with modified functional groups may be detected as they move along the strip by their fluorescent emission or detected when immobilized on a test line by molecules specific to binding the fluorescent nanocrystal with one or more modified functional groups. Illustrated in FIG. 9, is a non-limiting example of a lateral flow test strip 900 that can be used with one or more functional groups whose size can be changed that are bound in one embodiment to thermally stable imidazole coated fluorescent nanocrystals 908. For example, imidazole bound coated fluorescent nanocrystals can have one or more functional groups like telomeras primers bound to the coating to give particles 908 illustrated in FIG. 9. As shown in the schematic a test or sample material 904, which can be a cancer tissue or lysate, can be loaded onto a pad 912. The pad 912, which can be nylon or other compatible material can saturated with a working buffer, for example a telomerase working buffer, containing the fluorescent nanocrystal particles 908 and a size exclusion gel which may be a Sepharose gel. As a result of elongation of one or more of the functional groups, for example TS primer extension by telomerase, fluorescent nanoparticles with extended functional groups 916 preferably leave the (Sepharose) gel in the pad 912 and migrate through the membrane 930. The membrane 930 can be nitrocellulose or other chemically compatible and selective material for migrating the particles 916. Particles 908 with unchanged functional groups, for example TS primer strands, will stay in the pad 912 or have slower movement. The membrane 930 of the lateral flow strip 900 may have also include reading lines 920 or absorbent pads 924 that can include materials for selectively binding to the migrating fluorescent nanocrystal particles 916. For example, because extended telomeric strands have the ability to coil and form stable G-quadruplex structures, fluorescent nanoparticles with extended TS primers are able to bind to G-quadruplex-specific molecules embedded in the membrane 930 as a reading line 920. Several G-quadruplex binding compounds can be used such as, distamycin and telomestatin exhibited high specificity toward telomeric G-quadruplex. Designed aptamers (oligonucleotides developed by a SELEX in vitro evolution process) with high specificity to telomeric sequences can also be utilized for the reading line. Due to the high fluorescence intensity of FNCs, a hand held UV lamp can be used to illuminate the captured biosensor particles 916 on the reading line 924. For semi-quantitative detection of telomerase, several reading lines with various densities of telomere binding compounds can be imprinted on the membrane 930.

High throughput screening will greatly benefit large population diagnostics and anti-cancer drug discovery. Successful telomerase detection formats can be modified for adaptation to existing high throughput screening platforms. There are presently several commercially available high throughput instruments for 96-well fluorescence or polarization detection platforms. Flow cytometry analysis offers a promising resource for the use of telomerase biosensors in the diagnosis of different types of leukemia.

EXAMPLE 1

This prophetic example illustrates the preparation of functionalized fluorescent nanocrystals whose functional groups may be elongated or shortened by contact with a sample thereby resulting in a change in the spectral properties of the fluorescent nanocrystals.

Cadmium selenide core nanocrystals can be coated with a zinc sulfide inorganic shell using a protocol based on thermolytic reactions of precursors in coordinating solvents. A continuous flow process (U.S. Pat. No. 6,179,912) can be used for the production of core CdSe nanocrystals to specific size (color) and spectral characteristics. The synthesis can be performed based on reacting dimethyl cadmium with trioctylphosphine selenium (TOPSe) in a coordinating solvent (trioctylphosphine oxide, TOPO) at elevated temperature (~300° C.). The collected CdSe nanocrystals in TOP/TOPO solution can be coated with a shell of ZnS using diethyl zinc and bis(trimethylsilyl)sulfide in a coordinating solvent. Several FNCs sizes (colors) can be synthesized using this method.

Functionalization (organic coating and water solubilization) of synthesized nanocrystals. The surface chemistry can be modified according to the requirements for each detection format. CdSe/ZnS core/shell nanocrystals dissolved in organic solvent (pyridine/chloroform) can be functionalized by concentrated aqueous solutions of imidazole ligands. The extracted nanocrystals can then dialyzed against distilled water using dialysis membrane with a molecular weight cut off (MWCO) of about 10 kD in order to remove excess ligand and to permit the self-assembly of the imidazole ligand molecules to form a thin layer on the surface of the nanocrystal. This step can be followed by cross-linking the imidazole ligand molecules to form a stable encapsulating layer. Due to electronic interactions, this step produces a significant enhancement in the fluorescence efficiency of the nanocrystals. The coated FNCs can then washed with a suitable buffer using centrifugation filters with a MWCO at 10 kD. The crosslinked FNCs are expected to be highly water soluble, stabilized and equipped with surface carboxyl groups available for covalent linking with one or more ligands or functional groups for construction of functionalized nanocrystals whose spectral properties are expected to be changed by elongation or shortening of the ligands.

EXAMPLE 2

Linking one or more DNA Oligonucleotides to FNCs, 18 µM of a 26-base oligonucleotide, 5'-ACC CTA ACC CTA ACC CTA ACC CTA AC-3', (SEQ ID NO:1), equipped with an amine modified linker arm of 12 carbons at the 5' end was conjugated to 25 nM FNCs (532 nm emission). The reaction involved treatment with 3 mM ethyldimethylaminopropyl-carbodiimide (EDC) and 5 mM N-hydroxysulfosuccinimide (sulfo-NHS) in 1 ml phosphate buffered saline (PBS) for 1 hour at room temperature. UV absorbance was used to confirm the success of the linking reaction and to measure the number of linked DNA strands per particle. After washing by centrifugal filtration (tangential flow filtration, Millipore, 10 kD), the concentration of the DNA-FNCs conjugate was adjusted to the concentration of a known standard solution of FNCs (control). The UV absorbance (OD) difference at 260 nm between the DNA-FNCs conjugate and the control is attributed to the linked DNA FIG. 2. Since each OD unit represents ~25 µg/ml oligonucleotides, calculations indicated that ~170 nucleic acid units were linked to each particle of FNCs.

What is claimed:

1. A composition comprising:
   one or more fluorescent nanocrystals;
   a coating material comprising imidazole-containing molecules bonded by an imidazole group of the molecule to the surface of the fluorescent nanocrystals, wherein the imidazole-containing molecules each comprise at least one glycine, phenylalanine, or leucine group; and
   one or more functional groups bonded to the coating material; the functional group bonded at a first end to the coating of the fluorescent nanocrystal, the second end of the functional groups extending from the nanocrystal coating.

2. The composition of claim 1 further comprising one or more acceptors or donors linked to the functional groups bonded to the coating material, the linked acceptor or donor exchanging energy with the fluorescent nanocrystal.

3. The composition of claim 1 where the functional groups comprise polynucleotides, polypeptides, glycoproteins, polysaccharides, lipoproteins, or combinations of these.

4. The composition of claim 1 where the fluorescent nanocrystal coating further comprises a cross linking agent.

5. The composition of claim 1 where the fluorescent nanocrystal composition further comprises a buffer and the composition is at a temperature of about 37° or greater.

6. The composition of claim 1 where the fluorescent nanocrystal composition includes a transfecting agent and cells and wherein the functional groups bonded to the coating can be elongated or shortened in the cells.

7. The composition of claim 1 where the one or more functional groups comprise telomerase primers bonded to the coating material; the primers bonded at a first end to the coating of the nanocrystal, the second end of the primer extending from the nanocrystal coating, where the spectral or physical properties of the fluorescent nanocrystal are modified by sequential elongation of the primers when telomerase molecules are present in the sample.

8. The composition of claim 1 where reaction of one or more of the functional groups with one or more target molecules in a sample includes sequential elongation or shortening of the one or more functional groups.

9. The composition of claim 1 where the number of functional groups bonded to the coating is greater than about 100.

10. The composition of claim 1 where the coated fluorescent nanocrystals have a quantum yield of greater than 70%.

11. A method comprising:
contacting a sample with fluorescent nanocrystals, the fluorescent nanocrystals comprising a coating of imidazole-containing molecules bonded by one or more of the imidazole group to the surface of the fluorescent nanocrystals, wherein the imidazole-containing molecules each comprise at least one glycine, phenylalanine, or leucine group; and one or more functional groups bonded to the coating material; the functional groups bonded at a first end to the coating of the fluorescent nanocrystal, the second end of the functional groups extending from the nanocrystal coating;
where the spectral or physical properties of the fluorescent nanocrystal are modified by sequential reaction of one or more of the functional groups with one or more target molecules in a sample; and
correlating a change in the spectral or physical properties of the fluorescent nanocrystals in the sample with the sequential reaction of one or more of the functional groups with one or more target molecules in the sample.

12. The method of claim 11 where the target molecule is an enzyme.

13. The method of claim 11 where the reaction of the functional groups with target molecules results in sequential elongation or sequential shortening of the functional groups.

14. The method of claim 11 where the reaction of functional groups with target molecules results in the addition or removal of one or more acceptors or donors from the functional groups.

15. The method of claim 11 where the change in the spectral or physical properties of the fluorescent nanocrystals in the sample is related to the number of target molecules in the sample.

16. The method of claim 11 where the one or more functional groups comprise telomerase primers bonded to the coating material; the primers bonded at a first end to the coating of the nanocrystal, the second end of the primer extending from the nanocrystal coating, and where the change in the spectral or physical properties of the fluorescent nanocrystal are modified by sequential elongation of the primers reacting with a sample comprising telomerase molecules and nucleotides.

17. The method of claim 11 where reaction of the functional groups with the target molecules in the sample occurs at a temperature of about 20° C. or greater.

18. The method of claim 11 where the spectral property is energy transfer, Stokes shift, a polarization shift, or a combination of these.

19. The method of claim 11 where the one or more acceptors or donors linked to the functional groups bonded to the coating material exchange energy with the fluorescent nanocrystal.

20. The method of claim 16 where the nucleotides further include nucleotides with an acceptor or donor label.

21. The composition of claim 1 where each imidazole-containing molecule further comprises a histidine group.

22. The composition of claim 1 where the fluorescent nanocrystal coating is cross linked.

23. The composition of claim 1 where the composition is stable upon prolonged storage in an aqueous medium.

24. The method of claim 11 where each imidazole-containing molecule further comprises a histidine group.

* * * * *